(12) United States Patent
Young et al.

(10) Patent No.: US 11,110,246 B2
(45) Date of Patent: Sep. 7, 2021

(54) BREATHING ASSISTANCE APPARATUS

(75) Inventors: Alex Young, Auckland (NZ); Silvan Terence Butler, Auckland (NZ); Jonathan McLean Thomson, Auckland (NZ); Andrew Paul Maxwell Salmon, Auckland (NZ); Venkata Subbarao Potharaju, Auckland (NZ); Benjamin Wilson Casse, Auckland (NZ); Tak Ming Chung, Auckland (NZ); Sergiu Constantin Filip, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 477 days.

(21) Appl. No.: 13/500,628

(22) PCT Filed: Oct. 8, 2010

(86) PCT No.: PCT/NZ2010/000201
§ 371 (c)(1),
(2), (4) Date: Jun. 26, 2012

(87) PCT Pub. No.: WO2011/056080
PCT Pub. Date: May 12, 2011

(65) Prior Publication Data
US 2012/0266880 A1   Oct. 25, 2012

Related U.S. Application Data

(60) Provisional application No. 61/250,186, filed on Oct. 9, 2009, provisional application No. 61/267,270, filed on Dec. 7, 2009.

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0069* (2014.02); *A61M 16/024* (2017.08);
(Continued)

(58) Field of Classification Search
CPC .............. A61M 16/08; A61M 16/0816; A61M 16/0875; A61M 16/16; A61M 16/161; A62B 9/00
(Continued)

(56) References Cited

U.S. PATENT DOCUMENTS 4,302,640 A * 11/1981 Vicenzi ............. A61M 16/0051
128/202.22
5,072,728 A    12/1991 Pasternack
(Continued)

FOREIGN PATENT DOCUMENTS

EP   0 788 805   8/1997
EP   1 127 583   8/2001
(Continued)

OTHER PUBLICATIONS

Feb. 14, 2011 International Search Report for PCT Application No. PCT/NZ2010/000201 filed on Oct. 8, 2010.

*Primary Examiner* — LaToya M Louis
(74) *Attorney, Agent, or Firm* — Knobbe Martens Olson & Bear LLP

(57) ABSTRACT

A device for use as part of a breathing assistance system for providing gases to a user. The device may include a fan, an enclosure for receiving a humidification chamber or both. A user interface of the device can indicate the operating mode of the device, whether a peripheral device is connected and whether a gases conduit is correctly connected to the outlet of the device. A controller in the device may hide or block
(Continued)

options from the display of the user interface and may also initiate a power save mode when the device is powered by a battery.

19 Claims, 16 Drawing Sheets

(51) Int. Cl.
*A61M 16/08* (2006.01)
*A61M 16/00* (2006.01)

(52) U.S. Cl.
CPC ...... *A61M 16/0816* (2013.01); *A61M 16/109* (2014.02); *A61M 16/1075* (2013.01); *A61M 16/161* (2014.02); *A61M 2016/0027* (2013.01); *A61M 2016/0039* (2013.01); *A61M 2205/3368* (2013.01); *A61M 2205/3653* (2013.01); *A61M 2205/502* (2013.01); *A61M 2205/52* (2013.01); *A61M 2205/8206* (2013.01)

(58) Field of Classification Search
USPC ............ 128/203.12, 203.16–203.17, 204.14, 128/204.22
See application file for complete search history.

(56) References Cited

U.S. PATENT DOCUMENTS

| | | | |
|---|---|---|---|
| 5,661,231 | A | 8/1997 | Koskela |
| 5,865,171 | A * | 2/1999 | Cinquin .................. 128/203.12 |
| 5,927,274 | A | 7/1999 | Servidio et al. |
| 6,050,260 | A * | 4/2000 | Daniell et al. .......... 128/204.22 |
| 6,086,430 | A | 7/2000 | Amoni et al. |
| 6,360,741 | B2 | 3/2002 | Truschel |
| 6,983,341 | B1 | 1/2006 | Lim et al. |
| 7,111,624 | B2 * | 9/2006 | Thudor et al. ........... 128/203.16 |
| 2002/0056452 | A1 | 5/2002 | Brewer et al. |
| 2003/0062045 | A1 | 4/2003 | Woodring et al. |
| 2003/0066526 | A1 | 4/2003 | Thudor et al. |
| 2004/0016433 | A1 | 1/2004 | Estes et al. |
| 2007/0000491 | A1 | 1/2007 | Chalvignac |
| 2007/0169776 | A1 | 7/2007 | Kepler et al. |
| 2007/0210462 | A1 | 9/2007 | Felty |
| 2007/0265877 | A1 | 11/2007 | Rice et al. |
| 2007/0274693 | A1 | 11/2007 | Farbarik |
| 2008/0072896 | A1 * | 3/2008 | Setzer ................... A61M 16/00 128/200.24 |
| 2008/0072902 | A1 | 3/2008 | Setzer et al. |
| 2008/0149101 | A1 | 6/2008 | Becker et al. |
| 2008/0264413 | A1 * | 10/2008 | Doherty et al. ......... 128/202.27 |
| 2010/0006098 | A1 * | 1/2010 | McGinnis ............. A61M 16/00 128/204.23 |
| 2010/0071689 | A1 | 3/2010 | Thiessen |
| 2011/0142688 | A1 | 6/2011 | Chappel et al. |
| 2012/0022390 | A1 | 1/2012 | Unger |
| 2012/0118288 | A1 * | 5/2012 | Hunt et al. ............... 128/203.27 |
| 2012/0325215 | A1 * | 12/2012 | Levenick et al. ........ 128/205.23 |

FOREIGN PATENT DOCUMENTS

| | | |
|---|---|---|
| EP | 1 714 668 | 10/2006 |
| EP | 2 017 586 | 1/2009 |
| EP | 2 055 337 | 5/2009 |
| WO | WO 2002/026304 | 4/2002 |
| WO | WO 2004/112873 | 12/2004 |
| WO | WO 2005/086316 | 9/2005 |
| WO | WO 2006/050384 | 5/2006 |
| WO | WO 2007/019625 | 2/2007 |
| WO | WO 2009/011907 | 1/2009 |
| WO | WO 2009/087607 | 7/2009 |
| WO | WO 2010/003064 | 1/2010 |
| WO | WO 2010/014020 | 2/2010 |
| WO | WO 2010/028427 | 3/2010 |
| WO | WO 2010/031126 | 3/2010 |
| WO | WO 2010/044039 | 4/2010 |

* cited by examiner

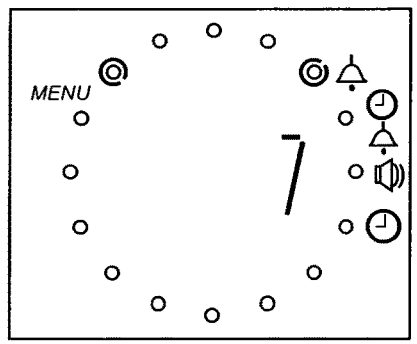
a.
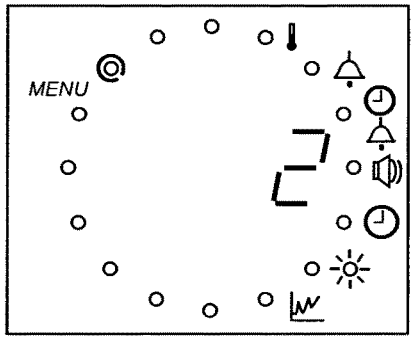
b.
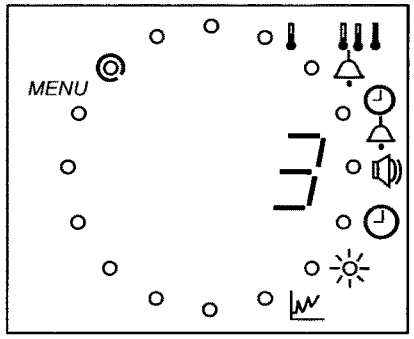
c.
FIGURE 5
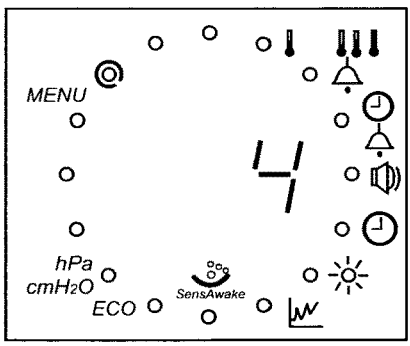
d.
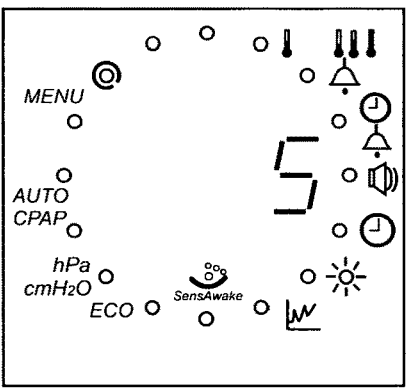
e.

BREATHING ASSISTANCE APPARATUS

BACKGROUND OF THE INVENTION

1. Field of the Invention

The present invention generally relates to a gases supply and gases humidification apparatus, particularly but not solely for providing respiratory assistance to patients or users who require a supply of humidified gas at positive pressure for the treatment of diseases such as Obstructive Sleep Apnea (OSA), snoring, or Chronic Obstructive Pulmonary Disease (COPD) and the like. More particularly, the present invention relates to a gases supply apparatus which has an integral humidifier chamber, so as to form a combined assisted breathing unit and humidifier.

2. Description of the Related Art

Devices or systems for providing a humidified gases flow to a patient for therapeutic purposes are available. Systems for providing therapy of this type, for example CPAP therapy, have a structure where gases at a required pressure are delivered from an assisted breathing unit or blower unit to a humidifier chamber downstream from the blower. As the gases pass through the humidifier chamber, they become saturated with water vapour. A flexible tubular gases conduit delivers the gases to a user or patient downstream from the humidifier chamber.

Humidified gases can be delivered from a modular system that has been assembled from separate units (i.e., a system where the humidifier chamber/heater and the breathing unit/blower are separate items) that are connected in series via conduits. An example of a system of this type is shown in FIG. 1. However, it is becoming more common for integrated blower/humidifier systems to be used. FIG. 2 shows an integrated blower/humidifier system.

An integrated system generally consists of a main blower or assisted breathing unit that provides a pressurised gas flow and a humidifier unit that mates with or is otherwise rigidly connected to the main blower unit. The mating occurs, for example, by a slide on or push connection so that the humidifier is held firmly in place on the main blower unit. An example of a system of this type is the Fisher and Paykel Healthcare 'slide-on' water chamber system shown and described in U.S. Pat. No. 7,111,624.

A general advantage of integrated devices is that they are more compact and discrete than a modular breathing circuit that has been assembled from separate units. A compact and discrete unit is particularly advantageous for home-use units, which are used where bedside space is limited and which may be transported and set up by a user elsewhere (e.g., if staying overnight away from home). The reduced footprint of an integrated unit tends to be less than modular units, which allows placement on a bedside stand or the like.

It is becoming more common for these types of devices to include a removable data storage device for storing data relating to, for example, use or compliance. The stored data then can be transported to another location via the removable data device for analysis or the like. Another advantage of removable data storage devices is that they can be used to provide set up parameters to a device, which parameters can be stored on the removable data device. Once the removable data device is connected to the breathing assistance unit, the set-up data can be downloaded into the memory of a controller on the breathing assistance unit. The set up parameters can be general parameters or the set up parameters can be tailored to an individual user. One problem with removably data storage devices is that they easily can be connected improperly or they easily can become at least partly disconnected during use. This improper connection or disconnection can occur in a manner that is not easily apparent to a user at first glance or that is not immediately or easily visually apparent.

Another problem with breathing assistance units of the type described above can occur with a connection between the static or bedside elements (e.g., the connection between the blower unit and the humidifier chamber) and the gases transportation pathway (e.g., a breathing conduit or hose) that connects between the static elements and a user interface. These items generally are formed in such a manner that the hose can be connected and disconnected multiple times for replacement or cleaning, for example.

Also, with some devices, the connection between the gases transportation pathway and the blower/humidifier unit requires an electrical connection to be made as well as a pneumatic connection. The wall or walls of some modern breathing conduits are integrally heated to reduce the likelihood of condensation, which is referred to as rain-out. The heating requires heater wires or heater elements in or on the conduit. The heating elements require power. There may also be sensors in the conduit that require an electrical connection to provide power and to provide a data transmission path. Incorrect connection or reconnection of the hose to the gases source units can cause pneumatic leaks, for example, or, if the system is of the type that has a pneumatic connection and an electrical connection, the necessary electrical contact can be intermittent or non-existent following connection or reconnection.

The use of a breathing assistance apparatus can be irritating to a user for a number of reasons: they can find prolonged wearing an interface uncomfortable or they (or their partner) can be disturbed by the operating noises of the apparatus. Such operating noises can include, for example, air escaping from an end of the hose or a relatively loud hissing noise made by the interface. There may also be induction noise as air is sucked into the system by the fan and the fan itself can be noisy when running. A major design consideration in domestic breathing assistance systems is minimizing the operating noise of the apparatus.

As breathing assistance apparatuses grow more complex and sophisticated, the control options have also increased in order to adjust output to produce the most effective therapy regime. Many efforts have been made to automate the operation of these devices. Accordingly, a great deal of the adjustment occurs automatically and 'behind-the-scenes' from the point of view of a user. However, a clinician or other health professional still will require a certain amount of manual control over an apparatus. For example, the clinician or other health profession will want to make initial set-up adjustments for a user or will want to tweak or adjust treatment parameters during regular check-ups. A clinician or other health professional will be trained in the operation of the machine, and due to this training, their professional background and their familiarity with types of breathing assistance apparatus, they will be comfortable with a greater degree of sophistication in control parameters and control displays. In contrast, the end user does not require this degree of control sophistication, and can easily become confused or overloaded if presented with too many options for adjusting or controlling the output.

Furthermore, some users travel extensively and regularly spend one or more consecutive nights away from home on business or pleasure. When travelling, a user may not have access to a mains power supply. For example, the user may need to sleep in their vehicle. In order to service this sector of the market, there are breathing assistance machines on the market that include an integral power supply or battery. Battery technology recently has developed to the point where batteries are small enough, light enough and powerful enough to be practical for this use. However, in normal operating mode, breathing assistance systems can use a large amount of power over an extended period, such as when running at full power for a full eight-hour sleep period. This sustained demand can easily drain batteries over the course of one or two nights.

Improved breathing assistance apparatuses that assist in overcoming one or more of the abovementioned disadvantages or that at least provide the public or industry with a useful choice are desired.

In this specification where reference has been made to patent specifications, other external documents, or other sources of information, such reference generally is for the purpose of providing a context for discussing certain features of the invention. Unless specifically stated otherwise, reference to such external documents is not to be construed as an admission that such documents, or such sources of information, in any jurisdiction, are prior art, or form part of the common general knowledge in the art.

BRIEF SUMMARY OF THE INVENTION

In some embodiments, the invention may include a blower unit for use as part of a breathing assistance system for providing gases to a user at a positive pressure for therapeutic purposes, comprising:

an outer casing, which encloses and forms part of said blower unit, said outer casing having an inlet vent or inlet port through which gases can enter said casing in use, and an outlet port, said inlet port and said outlet port connected by a gases path within said casing, a fan unit contained within said casing and located in said gases path, said fan unit adapted to receive said gases entering through said inlet vent and provide a pressurised gases stream to said outlet port, electronic circuitry enclosed within said casing, said electronic circuitry adapted to provide control signals to control the output or outputs of at least said blower unit, said blower unit further comprising a visual indicator adapted to indicate that the blower unit is in an operating mode.

The blower unit can further comprises a user display adapted to display information relating to the output or outputs of at least said blower, said visual indicator being part of said user display.

Alternatively, said visual indicator can be located on said casing and separate from said user display.

The visual indicator may be an LED.

The electronic circuitry may control the fan unit in multiple modes, including a plurality of operating modes in which the fan unit will supply gases at a positive therapeutic pressure, and at least one mode where the fan unit will not supply gases at a positive therapeutic pressure, and activates the same visual indicator in respect of all of the plurality of operating modes and does not activate the visual indicator in respect of other modes.

In other embodiments, the invention may include a gases modification unit for use as part of a breathing assistance system for providing gases to a user for therapeutic purposes, comprising:

an outer casing having an inlet vent or inlet port through which gases can enter said casing in use, and an outlet port, said inlet port and said outlet port connected by a gases path within said casing, electronic circuitry enclosed within said casing, said electronic circuitry adapted to provide control signals to control the modification of properties of gases passing along the gases path, said gases modification unit further comprising a connection display which is adapted to indicate to a user that a removable peripheral device is correctly connected to said blower unit in use.

The gases modification unit may further include a fan unit contained within said casing and located in said gases path. The fan unit may be adapted to receive said gases entering through said inlet vent and provide a pressurised gases stream to said outlet port.

The casing may have a slot or port on or within said casing and accessible from outside said casing, adapted to allow the connection of a removable memory device to said gases modification unit.

The connection display may be an LED offset from said slot or port.

The gases modification unit may further comprise a user display adapted to display information relating to operation of the gases modification unit and the connection display may be incorporated as part of said user display.

In other embodiments, the invention may include a gases modification unit and removable memory device for use as part of a breathing assistance system for providing gases to a user for therapeutic purposes, said unit comprising:

an outer casing, having an inlet vent or inlet port through which gases can enter said casing in use, and an outlet port, said inlet port and said outlet port connected by a gases path within said casing, electronic circuitry enclosed within said casing, said electronic circuitry adapted to provide control signals to control the modification of properties of gases passing along the gases path, the outer casing further comprising a slot or port on or within said casing and accessible from outside said casing, said slot and a removable memory device mutually adapted to allow the connection of said removable memory device to said blower unit in such a manner that when correctly connected, at least part of said removable memory device protrudes from said casing, said removable memory device further having a visual indicator on the outside surface, said visual indicator aligning with the edge of said slot when said removable memory device is correctly connected to said blower unit.

The visual indicator may be a line or ridge on the removable memory device.

The gases modification unit may include a fan unit contained within said casing and located in said gases path. The fan unit may be adapted to receive said gases entering through said inlet vent and provide a pressurised gases stream to said outlet port.

In other embodiments, the invention may include a gases modification unit for use as part of a breathing assistance system for providing heated humidified gases to a user at a positive pressure for therapeutic purposes, comprising:

an outer casing having an inlet vent or inlet port through which gases can enter said casing in use, and an outlet port adapted for connection to a gases conduit in use so that gases can pass out of said outlet port and into said conduit, said inlet port and said outlet port connected by a gases path within said casing, electronic circuitry enclosed within said casing, said electronic circuitry adapted to provide control signals to control the modification of properties of gases passing along the gases path, said gases modification unit further comprising a conduit connection display which is adapted to indicate to a user that said conduit is correctly connected to said outlet port.

The gases modification unit may include a fan unit contained within said casing and located in said gases path. The fan unit may be adapted to receive said gases entering through said inlet vent and provide a pressurised gases stream to said outlet port. The LED may be located on said casing at or close to said outlet port.

The gases modification unit may further comprise a user display adapted to display information relating to operation of the gases modification unit and the conduit connection display may be incorporated as part of said user display.

In other embodiments, the invention may include a gases modification unit for use as part of a breathing assistance system for providing gases to a user at a positive pressure for therapeutic purposes, comprising:

an outer casing having an inlet vent or inlet port through which gases can enter said casing in use, and an outlet port adapted for connection to a gases conduit in use so that gases can pass out of said outlet port and into said conduit, said inlet port and said outlet port connected by a gases path within said casing, electronic circuitry enclosed within said casing, said electronic circuitry adapted to provide control signals to control modification of properties of the gases passing through the gases path, a set of user controls adapted to allow a user to adjust operating parameters of the electronic circuitry, a user display, adapted to display a control menu which has a number of control and display options, said user controls manipulable to hide or block at least one and preferably a plurality of said control and display options, and once hidden, said user controls manipulable to unhide or unblock said control and display options.

Once said at least one of said control and display options is blocked, said user controls may be manipulable to hide or block further one or ones of said control and display options, and further manipulable to unhide or unblock said hidden one or ones of said control and display options.

The electronic circuitry may have a password-protection routine and the user controls require entry of a password before allowing a user to hide and unhide at least some of said control and display options.

The user controls may have a keying mechanism adapted to allow a user to hide and unhide at least some of said control and display options.

The gases modification unit may include a fan unit contained within said casing and located in said gases path, said fan unit adapted to receive said gases entering through said inlet vent and provide a pressurised gases stream to said outlet port.

In other embodiments, the invention may include a blower unit for use as part of a breathing assistance system for providing gases to a user at a positive pressure for therapeutic purposes, comprising:

an outer casing, which encloses and forms part of said blower unit, said outer casing having an inlet vent or inlet port through which gases can enter said casing in use, and an outlet port adapted for connection to a gases conduit in use so that gases can pass out of said outlet port and into said conduit, said inlet port and said outlet port connected by a gases path within said casing, a fan unit contained within said casing and located in said gases path, said fan unit adapted to receive said gases entering through said inlet vent and provide a pressurised gases stream to said outlet port, electronic circuitry enclosed within said casing, said electronic circuitry adapted to provide control signals to control the output or outputs of at least said blower unit, an internal power source contained within said casing and adapted to provide power to at least said fan unit and said electronic circuitry, said blower unit further adapted to connect to a mains supply to receive power for at least said fan unit and said electronic circuitry, in use, said blower unit drawing power from said mains supply by default if connected to said mains supply, and otherwise drawing power from said internal power source, the electronic circuitry including a power saving mode for operating the blower where work is done at a maximum power rate below the rate at which said blower unit draws power when connected to said mains supply.

The electronic circuitry may automatically switches to said power-saving mode when said blower unit is drawing power from said internal power source.

Alternatively, the blower unit may further comprise user controls adapted to allow a user to switch said electronic circuitry between a normal operating mode where full power is available, and said power-saving mode.

In some embodiments, when in said power saving mode, said maximum power rate is between 50 W and 100 W, or approximately 75 W.

In other embodiments, the invention may include a blower unit for use as part of a breathing assistance system for providing gases to a user at a positive pressure for therapeutic purposes, comprising:

an outer casing, which encloses and forms part of said blower unit, said outer casing having an inlet vent or inlet port through which gases can enter said casing in use, and an outlet port adapted for connection to a gases conduit in use so that gases can pass out of said outlet port and into said conduit, said inlet port and said outlet port connected by a gases path within said casing, a fan unit contained within said casing and located in said gases path, said fan unit adapted to receive said gases entering through said inlet vent and provide a pressurised gases stream to said outlet port, electronic circuitry enclosed within said casing, said electronic circuitry adapted to provide control signals to control the output or outputs of at least said blower unit, said blower unit further adapted to connect to an external power supply to receive power for at least said fan unit and said electronic circuitry, operate in a standard mode when connected to an AC mains power source, said electronic circuitry having a power saving mode where work is done at a maximum power rate below the rate at which said blower unit draws power when operating in said standard mode, said electronic circuitry adapted to detect when said blower unit is connected to a synthesised mains AC power supply.

The electronic circuitry may be adapted to detect the frequency of said synthesised mains AC power supply, said electronic circuitry automatically switching to said power-saving mode when said frequency is above 50 Hz.

Alternatively, or as well, said electronic circuitry may be adapted to detect the frequency of said synthesised mains AC power supply, said electronic circuitry automatically switching said to said power-saving mode when said frequency is above 60 Hz.

Alternatively, or as well, said electronic circuitry may be adapted to detect a secondary signal superimposed over the power supply signal, and to automatically switch to said power-saving mode on receipt of said secondary signal.

Alternatively, or as well, the blower unit may include a remote transmission detector connected to said electronic circuitry, said detector adapted to receive a transmitted signal and pass said signal to said electronic circuitry, said electronic circuitry switching to said power-saving mode in response to receiving a signal indicating that said blower unit is connected to a synthesised power supply.

In some embodiments, the blower unit may include user controls adapted to allow a user to manually switch said blower unit between said standard operating mode, and said power-saving mode.

In some embodiments, the power saving mode, said maximum power rate is between 50 W and 100 W, or about 75 W.

In other embodiments, the invention may include a blower unit for use as part of a breathing assistance system for providing gases to a user at a positive pressure for therapeutic purposes, comprising:

an outer casing, which encloses and forms part of said blower unit, said outer casing having an inlet vent or inlet port through which gases can enter said casing in use, and an outlet port adapted for connection to a gases conduit in use so that gases can pass out of said outlet port and into said conduit, said inlet port and said outlet port connected by a gases path within said casing, a fan unit contained within said casing and located in said gases path, said fan unit adapted to receive said gases entering through said inlet vent and provide a pressurised gases stream to said outlet port, electronic circuitry enclosed within said casing, said electronic circuitry adapted to provide control signals to control the output or outputs of at least said blower unit, an internal power source contained within said casing and adapted to provide power to at least said fan unit and said electronic circuitry, said blower unit further adapted to connect to a mains supply to receive power for at least said fan unit and said electronic circuitry, in use, said blower unit drawing power from said mains supply by default if connected to said mains supply, and otherwise drawing power from said internal power source, said electronic circuitry having a power saving mode where work is done at a maximum power rate below the rate at which said blower unit draws power when connected to said mains supply, said blower unit further comprising user controls adapted to allow a user to switch said electronic circuitry between a normal operating mode where full power is available, and said power-saving mode.

The electronic circuitry may automatically switch to said power-saving mode when said blower is drawing power from said internal power source, said user controls further adapted to allow a user to switch said blower unit from said power saving mode to said normal operating mode manually when said blower unit is drawing power from said internal power source.

In some embodiments, when said blower is in said power saving mode, said maximum power rate is between 50 W and 100 W, or about 75 W.

In other embodiments, the invention may include a gases modification unit for providing heated humidified gases to a user, said system using a humidifier chamber of the type which in use contains a volume of water and which has a humidifier gases inlet and a separate humidifier gases outlet, said unit comprising:

an outer casing, which encloses and forms part of said unit, said outer casing having an inlet vent or inlet port through which gases can enter said casing in use, a patient outlet mounted on said casing and adapted for connection to a gases conduit in use so that gases can pass out of said patient outlet and into said conduit, an enclosure adapted to in use receive said humidifier chamber, said enclosure having an inlet port adapted to in use align with said humidifier gases inlet, an outlet gases passage, in use said outlet gases passage running between and gaseously connecting said humidifier gases outlet and said patient outlet so that heated humidified gases exiting said humidifier chamber pass into said patient outlet, said outlet gases passage formed as a separate item to said casing and said enclosure, at least part of said outlet gases passage accessible from within said enclosure and adapted to allow a user to remove and replace said outlet gases passage easily.

The outlet gases passage may have the overall form of a funnel, an inner portion of said outlet gases passage forming a mouth of said funnel, an outer portion of said outlet gases passage forming a stem of said funnel. The mouth of the funnel may be substantially rectangular.

The mouth of the funnel may be surrounded by a flange. At least a portion of said stem of the funnel may be wider than a remainder of the stem. The wider portion may be formed at the outer rim of said stem, said rim having a barbed appearance in cross-section.

The gases modification unit may include a fan unit contained within said casing, said fan unit adapted to receive said gases entering through said inlet vent and provide a pressurised gases stream to said enclosure inlet port.

The gases modification unit may include a heater located in said enclosure, in use said heater contacting the humidifier chamber to heat said volume of water.

In other embodiments, the invention may include a gases modification unit for providing heated humidified gases to a user, said system using a humidifier chamber of the type which in use contains a volume of water and which has a humidifier gases inlet and a separate humidifier gases outlet, said blower unit comprising:

an outer casing, which encloses and forms part of said blower unit, said outer casing having an inlet vent or inlet port through which gases can enter said casing in use, a patient outlet mounted on said casing and adapted for connection to a gases conduit in use so that gases can pass through and out of said patient outlet and into said conduit, an enclosure adapted to in use receive said humidifier chamber, said enclosure having an inlet port adapted to in use align with said humidifier gases inlet, an outlet gases passage, in use said outlet gases passage running between and gaseously connecting said humidifier gases outlet and said patient outlet so that heated humidified gases exiting said humidifier chamber pass into said patient outlet, said patient outlet removably mounted on said casing.

The patient outlet may be an elbow connector.

In some embodiments, the patient outlet may be a substantially right-angled elbow connector.

Alternatively, or as well, the patient outlet may be a gases passage having an inner end and an outer end, said inner end adapted to connect to said casing and receive a stream of heated, humidified gases from said integrated blower/humidification system, said outer end adapted to in use connect to a gases conduit, said patient outlet may also have an insulating wall formed around and spaced from at least said inner end so that an airgap is formed between said inner end of said gases passage and said insulating wall.

The patient outlet may also have a recess formed on the inner side of the bend of the elbow.

The gases modification unit may include a fan unit contained within said casing, said fan unit adapted to receive said gases entering through said inlet vent and provide a pressurised gases stream to said enclosure inlet port.

The gases modification unit may include a heater located in said compartment, in use said heater contacting said humidification chamber to heat said volume of water.

In other embodiments, the invention may include a patient connector for use as part of a gases modification unit for providing heated humidified gases to a user, said blower unit of the type that has an outer casing, said patient connector comprising:

a gases passage having an inner end and an outer end, said inner end adapted to connect to said casing and receive a stream of heated, humidified gases from said gases modification unit, said outer end adapted to in use connect to a gases conduit, an insulating wall, formed around and spaced from at least said inner end so that an insulating space is formed between said inner end of said gases passage and said insulating wall.

The patient outlet may be an elbow connector. In some embodiment, the patient outlet may be a substantially right-angled elbow connector.

The patient outlet may also have a recess formed on the inner side of the bend of the elbow.

In other embodiments, the invention may include a humidifier unit for use with a system for providing humidified gases to a user, comprising:

a humidifier chamber adapted to contain a volume of water, said humidifier chamber further having a gases inlet port and a gases outlet port, an elongate inlet passage extending into said humidifier chamber from said gases inlet port, said inlet passage having at least one primary gases inlet aperture, at or towards that end of said inlet passage furthest from said gases inlet, to allow gases to pass out of said inlet passage and into said humidifier chamber, an elongate exit passage extending into said humidifier chamber from said gases outlet port, said passage having at least one and preferably two primary gases exit apertures, at or towards that end of said exit passage furthest from said gases outlet, to allow gases to pass out of said humidifier chamber and into said exit passage, said primary gases inlet aperture formed in the side of said inlet passage.

The primary gases exit aperture or apertures may be formed in the side or sides of said exit passage.

The elongate inlet passage may have an inlet recess formed in the lower part of said inlet passage, and at least one and preferably a plurality of secondary inlet apertures formed in said recess to allow gases to pass out of said inlet passage and into said humidifier chamber.

The elongate exit passage may have an exit recess formed in the lower part of said inlet passage, and at least one and preferably a plurality of secondary exit apertures formed in said recess to allow gases to pass out of said humidifier chamber and into said exit passage.

In some embodiment, the exit passage and said entry passage may be aligned at an angle to one another.

The primary gases inlet aperture may be formed in that side of said inlet passage which is furthest from said exit passage.

The chamber may have at least one and preferably a plurality of buttress ribs spanning between the wall of said humidifier chamber and a position at or close to the inner end of at least one of said exit passage or said entry passage. The buttress rib or ribs may be located at or towards the top of said chamber.

In some embodiments, the chamber may appear substantially circular in plan view.

In some embodiments, the exit passage, the entry passage and said buttress ribs may be arranged radially and connect at the centre of said chamber, the inner ends of said exit passage and said entry passage blocked by a dividing wall.

The chamber may have a baffle which extends downwards between said entry passage and said exit passage.

The humidifier chamber may be open-topped, and said humidifier unit also have a separate lid unit, adapted to close and seal said open top of said humidifier chamber in use.

The lid unit may comprise a separate lid portion and a handle portion, said handle portion releasably connecting to said lid portion in such a manner that said handle can freely rotate while connected to said lid portion, said lid portion adapted to seal on said open top of said humidifier chamber.

In some embodiments, the inlet passage and said exit passage are structurally connected but fluidically disconnected.

In other embodiments, the invention may include a humidifier unit for use with a system for providing humidified gases to a user, comprising:

a humidifier chamber adapted to contain a volume of water, said humidifier chamber further having a gases inlet port and a gases outlet port, an elongate inlet passage extending into said humidifier chamber from said gases inlet port, said inlet passage having at least one primary gases inlet aperture, at or towards that end of said inlet passage furthest from said gases inlet, to allow gases to pass out of said inlet passage and into said humidifier chamber, an elongate exit passage extending into said humidifier chamber from said gases outlet port, said passage having at least one and preferably two primary gases exit apertures, at or towards that end of said exit passage furthest from said gases outlet, to allow gases to pass out of said humidifier chamber and into said exit passage, at least one of said primary gases exit apertures formed in the side of said exit passage.

The primary gases inlet aperture may be formed in the side of said inlet passage.

The elongate inlet passage may have an inlet recess formed in the lower part of said inlet passage, and at least one and preferably a plurality of secondary inlet apertures formed in said recess to allow gases to pass out of said inlet passage and into said humidifier chamber.

The elongate exit passage may have an exit recess formed in the lower part of said exit passage, and at least one and preferably a plurality of secondary exit apertures formed in said exit recess to allow gases to pass out of said humidifier chamber and into said exit passage.

In some embodiments, the exit passage and said entry passage may be aligned at an angle to one another.

The primary gases inlet aperture may be formed in that side of said inlet passage which is furthest from said exit passage.

The chamber may have also has at least one and preferably a plurality of buttress ribs spanning between the wall of said humidifier chamber and a position at or close to the inner end of at least one of said exit passage or said entry passage. The buttress rib or ribs may be located at or towards the top of said chamber.

In some embodiments, the chamber may appear substantially circular in plan view.

In some embodiments, the exit passage, said entry passage and said buttress ribs may be arranged radially and connect at the centre of said chamber, the inner ends of said exit passage and said entry passage blocked by a dividing wall.

The chamber may have a baffle which extends downwards between said entry passage and said exit passage.

The humidifier chamber may be open-topped, and said humidifier unit may have a separate lid unit, adapted to close and seal said open top of said humidifier chamber in use.

The lid unit may comprise a separate lid portion and a handle portion, said handle portion releasably connecting to said lid portion in such a manner that said handle can freely rotate while connected to said lid portion, said lid portion adapted to seal on said open top of said humidifier chamber.

The inlet passage and the exit passage may be structurally connected but fluidically disconnected.

In other embodiments, the invention may include a humidifier unit for use with a system for providing humidified gases to a user, comprising:

a humidifier chamber adapted to contain a volume of water, said humidifier chamber further having a gases inlet port and a gases outlet port, an inlet passage extending into said humidifier chamber from said gases inlet port, an exit passage extending into said humidifier chamber from said gases outlet port, at least one of said passages having a recess formed in the lower part of said passage or passages, at least one and preferably a plurality of apertures formed in said recess to allow gases to pass between said passage and said chamber.

The inlet passage may be an elongate passage extending into said humidifier chamber from said gases inlet port. The recess may be formed in said inlet passage. The at least one and preferably a plurality of apertures may be secondary gases inlet apertures. The inlet passage may also have at least one primary gases inlet aperture, at or towards that end of said inlet passage furthest from said gases inlet, to allow gases to pass out of said inlet passage and into said humidifier.

The exit passage may be an elongate exit passage extending into said humidifier chamber from said gases outlet port. The exit passage may have at least one and preferably two primary gases exit apertures, at or towards that end of said exit passage furthest from said gases outlet, to allow gases to pass out of the humidifier chamber and into said exit passage.

The exit passage may be an elongate passage extending into said humidifier chamber from said gases exit port. An exit recess may be formed in said exit passage, with said at least one and preferably a plurality of apertures being secondary gases exit apertures. The exit passage may also have at least one primary gases exit aperture, at or towards that end of said exit passage furthest from said gases exit port, to allow gases to pass out of said humidifier chamber and into said exit passage.

The inlet passage may be an elongate passage extending into said humidifier chamber from said gases inlet port. The passage may have at least one gases inlet aperture, at or towards that end of said inlet passage furthest from said gases inlet port, to allow gases to pass into said humidifier chamber from said inlet passage.

The primary gases inlet aperture may be formed in the side of said inlet passage.

The primary gases exit aperture or apertures may be formed in the side or sides of said exit passage.

The elongate exit passage may also have an exit recess formed in the lower part of said exit passage. At least one and preferably a plurality of secondary exit apertures may be formed in said exit recess to allow gases to pass out of said humidifier chamber and into said exit passage.

The exit passage and the entry passage may be aligned at an angle to one another.

The primary gases inlet aperture may be formed in that side of said inlet passage which is furthest from said exit passage.

The chamber may also have at least one and preferably a plurality of buttress ribs spanning between the wall of said humidifier chamber and a position at or close to the inner end of at least one of said exit passage or said entry passage. The buttress rib or ribs may be located at or towards the top of said chamber.

In some embodiments, the chamber may be substantially circular in plan view.

The exit passage, said entry passage and said buttress ribs may be arranged radially and connect at the centre of said chamber, with the inner ends of said exit passage and said entry passage blocked by a dividing wall.

The chamber may have a baffle which extends downwards between said entry passage and said exit passage.

The humidifier chamber may be open-topped, and the humidifier unit may have a separate lid unit, adapted to close and seal said open top of said humidifier chamber in use. The lid unit may comprise a separate lid portion and a handle portion, said handle portion releasably connecting to said lid portion in such a manner that said handle can freely rotate while connected to said lid portion, said lid portion adapted to seal on said open top of said humidifier chamber.

In other embodiments, the invention may include a humidifier unit for use with a system for providing humidified gases to a user, comprising:

a humidifier chamber adapted to contain a volume of water, said humidifier chamber further having a gases inlet port and a gases outlet port, an elongate inlet passage extending into said humidifier chamber from said gases inlet port, said inlet passage having at least one gases inlet aperture, at or towards that end of said inlet passage furthest from said gases inlet, to allow gases to pass out of said inlet passage and into said humidifier chamber, an elongate exit passage extending into said humidifier chamber from said gases outlet port, said passage having at least one gases exit apertures, at or towards that end of said exit passage furthest from said gases outlet, to allow gases to pass out of said humidifier chamber and into said exit passage, said chamber also has at least one and preferably a plurality of buttress ribs spanning between the wall of said humidifier chamber and a position at or close to the inner end of at least one of said exit passage or said entry passage.

The buttress rib or ribs may be located at or towards the top of said chamber.

In some embodiments, at least one of said passages may have a recess formed in the lower part of said passage or passages, with at least one and preferably a plurality of apertures formed in said recess or recesses to allow gases to pass between said passage and said chamber.

The inlet passage may be an elongate passage extending into said humidifier chamber from said gases inlet port, with said recess formed in said inlet passage. The at least one aperture may be secondary gases inlet apertures. The inlet passage may also have at least one primary gases inlet aperture, at or towards that end of said inlet passage furthest from said gases inlet, to allow gases to pass out of said inlet passage and into said humidifier chamber.

The exit passage may be an elongate exit passage extending into said humidifier chamber from said gases outlet port, said passage having at least one and preferably two primary gases exit apertures, at or towards that end of said exit passage furthest from said gases outlet, to allow gases to pass out of said humidifier chamber and into said exit passage.

An exit recess may be formed in said exit passage, at least one and preferably a plurality of secondary gases exit apertures formed in said recess, to allow gases to pass out of said humidifier chamber and into said exit passage.

In some embodiments, said primary gases inlet aperture may be formed in the side of said inlet passage.

The primary gases exit aperture or apertures may be formed in the side or sides of said exit passage.

The exit passage and said entry passage may be aligned at an angle to one another. The primary gases inlet aperture may be formed in that side of said inlet passage which is furthest from said exit passage.

In some embodiments, the chamber may appear substantially circular in plan view.

In some embodiments, the chamber further may have a baffle which extends downwards between said entry passage and said exit passage.

In some embodiments, the humidifier chamber may be open-topped, and said humidifier unit may have a separate lid unit, adapted to close and seal said open top of said humidifier chamber in use. The lid unit may comprise a separate lid portion and a handle portion, said handle portion releasably connecting to said lid portion in such a manner that said handle can freely rotate while connected to said lid portion, said lid portion adapted to seal on said open top of said humidifier chamber.

In other embodiments, the invention may include a humidifier unit for use with a system for providing humidified gases to a user, comprising:

a humidifier chamber adapted to contain a volume of water, an inlet passage having a gases inlet port adapted to receive gases from a gases source in use, and at least one gases inlet aperture adapted to allow gases to pass out of said inlet passage and into said humidifier chamber, an exit passage having a gases outlet port adapted to allow said heated humidified gases to exit said chamber, and at least one gases exit aperture adapted to allow gases to pass out of said humidifier chamber and into said exit passage, in plan view, said gases inlet aperture and said gases exit aperture located at or close to the centre of said chamber, and said gases outlet port and said gases inlet port are located inside the perimeter of said chamber.

The gases outlet port and said gases inlet port may be located at or close to close to the centre of said chamber. The gases outlet port may be located between said perimeter and said gases exit aperture, and said gases inlet port may be located between said perimeter and said at least one gases inlet aperture.

In some embodiments, the humidifier unit also has at least one and preferably a plurality of buttress ribs spanning between the wall of said humidifier chamber and said inlet passage and said exit passage, said inlet passage and said exit passage unconnected to said chamber except via said ribs. The buttress rib or ribs and said passages are located at or towards the top of said chamber. The chamber may appear substantially circular in plan view, said passages extending radially towards the perimeter of said chamber, said passages structurally connected at the centre of said chamber but gaseously or fluidically unconnected. The buttress rib or ribs may extend radially from said passages to the perimeter of said chamber. The gases outlet port is aligned substantially horizontally. Alternatively, gases outlet port may be aligned facing upwards substantially vertically.

In some embodiments, the gases inlet port may be aligned substantially horizontally.

Alternatively, the gases inlet port may be aligned facing upwards substantially vertically.

In some embodiments, the inlet passage may be an elongate passage having at least one primary gases inlet aperture, at or towards that end of said inlet passage furthest from said gases inlet, formed in the side of said inlet passage, to allow gases to pass out of said inlet passage and into said humidifier chamber.

In some embodiment, the exit passage may be an elongate exit passage having at least one and preferably two primary gases exit apertures, at or towards that end of said exit passage furthest from said gases outlet, formed in the side or sides of said exit passage to allow gases to pass out of said humidifier chamber and into said exit passage.

In some embodiments, at least one of said passages may have a recess formed in the lower part of said passage or passages, at least one and preferably a plurality of secondary apertures formed in said recess or recesses to allow gases to pass between said passage and said chamber.

In some embodiments, said exit passage and said entry passage may be aligned at an angle to one another. The primary gases inlet aperture may be formed in that side of said inlet passage which is furthest from said exit passage.

In some embodiments, said chamber may have a baffle which extends downwards between said entry passage and said exit passage.

In some embodiments, said humidifier chamber may be open-topped, and said humidifier unit may have a separate lid unit, adapted to close and seal said open top of said humidifier chamber in use. The lid unit may comprise a separate lid portion and a handle portion, said handle portion releasably connecting to said lid portion in such a manner that said handle can freely rotate while connected to said lid portion, said lid portion adapted to seal on said open top of said humidifier chamber.

In other embodiments, the invention may include a gases modification unit for use as part of a breathing assistance system for providing gases to a user at a positive pressure for therapeutic purposes, comprising:

an outer casing having an inlet vent or inlet port through which gases can enter said casing in use, and an outlet port adapted for connection to a gases conduit in use so that gases can pass out of said outlet port and into said conduit, said inlet port and said outlet port connected by a gases path within said casing, electronic circuitry enclosed within said casing, said electronic circuitry adapted to provide control signals to control modification of properties of the gases passing through the gases path, a set of user controls adapted to allow a user to adjust operating parameters of the electronic circuitry, a user display, adapted to display a control menu which has a number of control and display options, said electronic circuitry adapted to selectively not respond to manipulations of the user controls.

The electronic circuitry may stop responding to manipulations of the user controls after a predetermined period of time without manipulation of the controls.

Alternatively, the electronic circuitry will stop responding to manipulations of the user controls after a predetermined period of time without manipulation of the controls, when in one or more predetermined operating modes.

Alternatively, or additionally, the electronic circuitry will stop responding to manipulations of the user controls after a predetermined period of time without manipulation of the controls, but will still respond when in one or more predetermined operating modes.

In some embodiments, the gases modification unit may include a fan unit contained within said casing and located in said gases path, said fan unit adapted to receive said gases entering through said inlet vent and provide a pressurised gases stream to said outlet port.

The term "comprising" as used in this specification means "consisting at least in part of," that is to say when interpreting statements in this specification which include that term, the features, prefaced by that term in each statement, all need to be present but other features can also be present.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

These and other features, aspects and advantages of an improved breathing assistance apparatus will now be described with reference to the drawings of a preferred embodiment, which embodiment is intended to illustrate and not to limit the invention, and in which figures:

FIGS. 5a-5e show examples of displays that can be shown on the user display panel of the blower unit with FIG. 5e showing the maximum amount of information that can be displayed on the illustrated user display and FIGS. 5a-d showing displays having different combinations of the information blocked so that it is not viewed by a user.

DETAILED DESCRIPTION OF THE INVENTION

Figure 1:
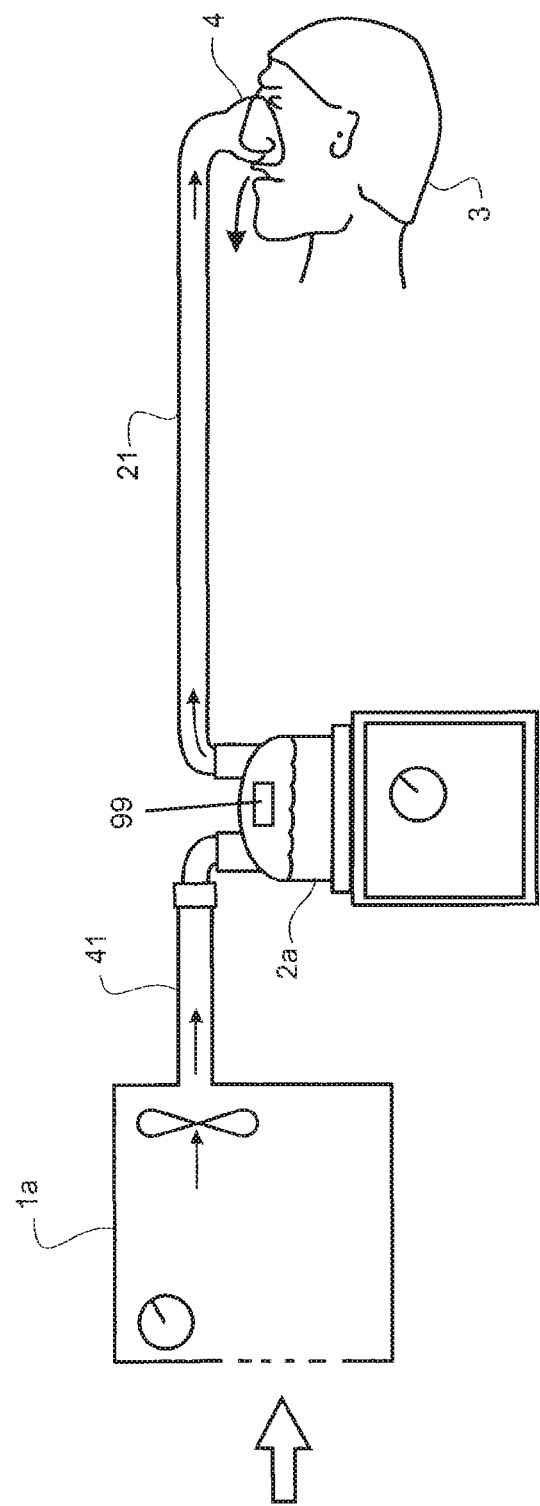
FIG. 1 shows a schematic view of a user receiving humidified air from a modular breathing assistance apparatus.

A schematic view of a user 3 receiving air from a modular assisted breathing unit and humidifier system is shown in FIG. 1. A conduit 41 provides pressurised air from an assisted breathing unit or blower 1a to a humidifier chamber 2a. Humidified, heated and pressurised gases exit the humidifier chamber 2a via a conduit 21, and are provided to the patient or user 3 via a user interface 4. The user interface 4 shown in FIG. 1 is a nasal mask, which covers the nose of the user 3. However, it should be noted that in systems of these types, a full face mask, nasal cannula, tracheostomy fitting nasal pillows, oral interface, or any other suitable user interface could be substituted for the nasal mask shown.

Figure 2:
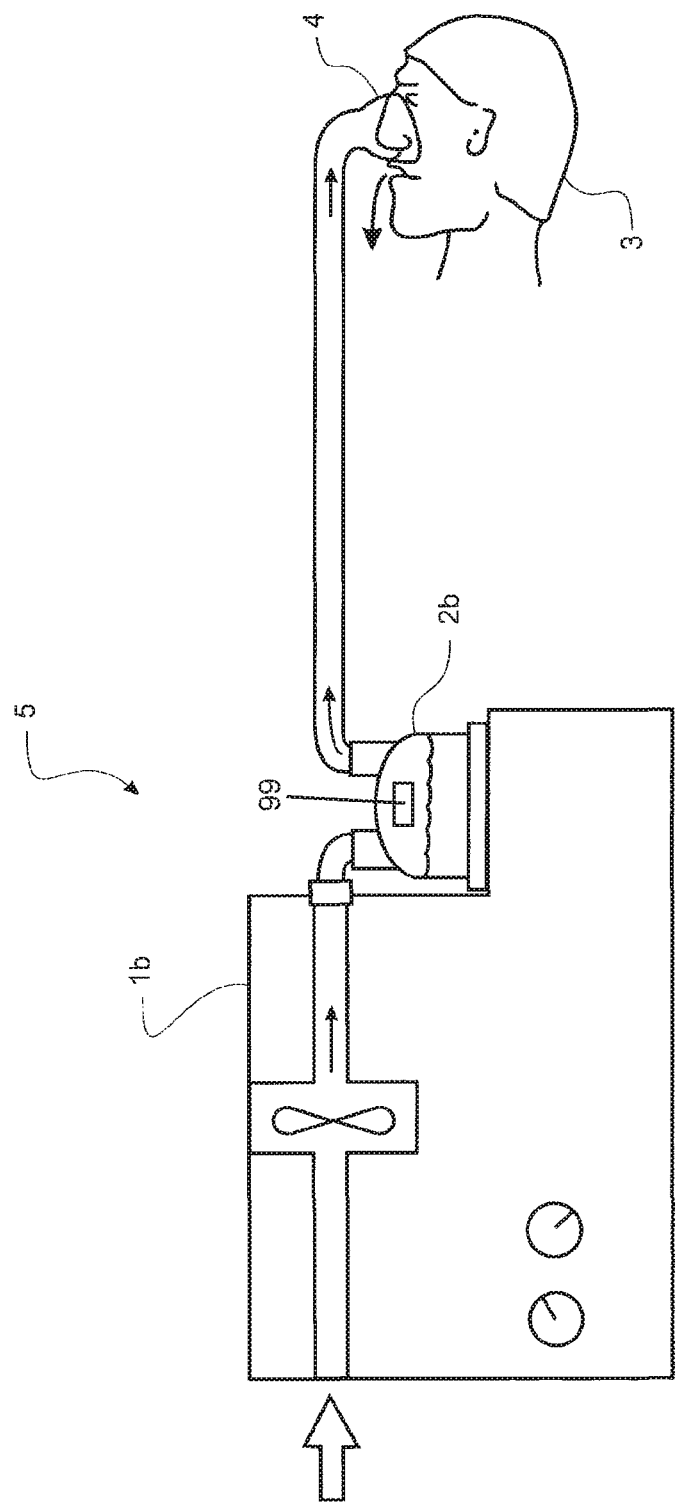
FIG. 2 shows a schematic view of a user receiving humidified air from an integrated breathing assistance apparatus.

FIG. 2 shows a schematic view of the user 3 receiving air from an integrated blower/humidifier unit 5. The system generally operates in the same manner as the modular system shown in FIG. 1 except that a humidifier chamber 2b has been integrated with a blower unit 1b to form the integrated unit 5. An example of an integrated unit is described in PCT application WO2008/056993, which is hereby incorporated by reference in its entirety.

Assisted Breathing Unit

An improved form of an assisted breathing unit or integrated unit 6 will now be described with reference to FIGS. 3 and 4.

The integrated unit 6 comprises two main parts: an assisted breathing or blower unit 7 and a humidification unit 31. When in use, the humidification unit 31 generally is enclosed within an enclosure 42 that is formed in an external casing of the integrated unit 6. In the illustrated configuration, the top part of the humidication unit 31 is not enclosed within the enclosure 42.

The blower unit 7 has an outer shell that generally is a rectangular block with substantially vertical side and rear walls, and a front face that is angled slightly rearwards. In the illustrated embodiment, the walls, base and top surface are all manufactured and connected as far as possible to minimise the occurrence of seams. Any necessary seams can be sealed. This outer shell generally encloses the working parts of the blower unit 7 and forms part of the blower unit 7.

Figure 3:
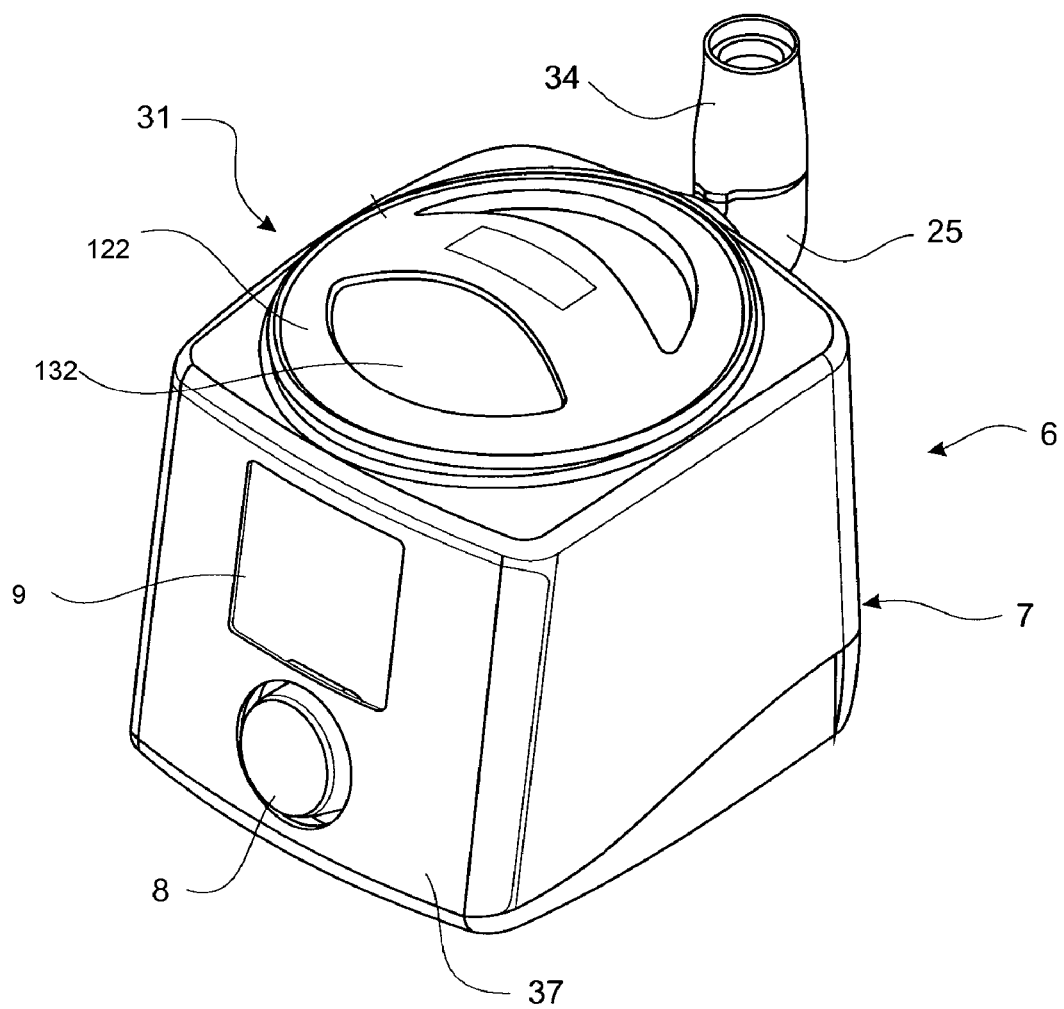
FIG. 3 shows an embodiment of a blower and humidifier of a breathing assistance apparatus that is arranged and configured in accordance with certain features, aspects and advantages of the present invention. The illustrated apparatus is of the integrated blower/humidifier type and includes a blower unit that has a central enclosure that receives a humidifier. The blower unit also has a front face with a user display panel and user controls.
Figure 4:
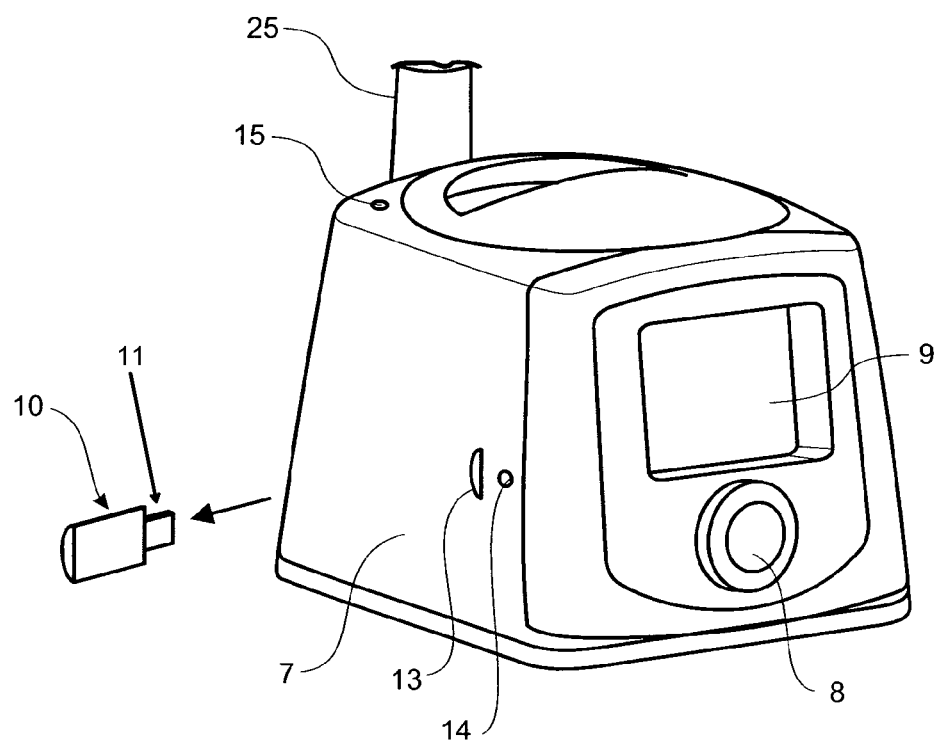
FIG. 4 shows a different view of breathing assistance apparatus of FIG. 3 with detail of a slot that receives a removable memory device shown and the removable memory device suitable for use with the integrated blower/humidifier system also shown.

As shown in FIGS. 3 and 4, a user interface is located on the lower section of the front face of the illustrated integrated unit 6 with a control display 9 located directly above the user interface. The user interface can include a control knob 8. A patient outlet 25 is shown passing out of the rear wall of the integrated unit 6. In the illustrated embodiment, in use the free end of the outlet 25 faces upwards for ease of connection. However, the patient outlet 25 can be rotated to one side or to the other side to move or align it in a more convenient position for storage or to provide a more convenient use position.

The illustrated patient outlet 25 is adapted to allow both pneumatic and electrical connection to one end of a conduit, e.g., the conduit 21, that extends between the unit 6 and a patient interface, e.g., the interface 4. An example of the type of connector that can be used and the type of dual connection that can be made is described in U.S. Pat. No. 6,953,354, which is hereby incorporated by reference in its entirety. It should be noted that for the purposes of reading this specification, the patient interface generally can be thought of as including both the interface 4 and the conduit 21 where it would be appropriate to read it in this manner.

The currently preferred embodiment of integrated unit 6 includes an inlet vent or inlet port (not shown) to draw air in from atmosphere. In alternative embodiments, the inlet port or vent could be a connector adapted to receive gases from a wall source, pressure bottle or the like. The integrated unit 6 can also include a mechanism for providing a pressurised air flow from the inlet vent to the humidifier chamber, which, in some embodiments, is a fan unit that acts as a pressurised air flow mechanism. The vent can be located wherever is convenient on the external surface of the integrated unit 6. In some embodiments, it is located on the rear face of the blower unit 7.

The air is ducted or otherwise directed along an air path through the casing of the blower unit 7 and delivered to the humidifier chamber 12, where it is humidified and heated, before passing out of the humidification unit 31 and onwards to the patient outlet 25 on the blower unit 7. The heated humidified gas then passes to the user 3 via the conduit 21.

The outlet port or patient outlet 25 is adapted to enable both pneumatic attachment of the patient conduit 21 and electrical connection via an electrical connector. In FIG. 3, a conduit connector 34 that would normally be fitted to the end of the conduit 21 is shown connected to the patient outlet 25. The outlet port or outlet connection does not have to be via the housing of the integrated unit 6, as in the illustrated embodiment. Instead, the connection for the conduit 21 could be located directly on an outlet from humidifier chamber 12. The illustrated form and variations generally can be referred to as connection mechanisms.

The blower unit 7 also contains electronic circuitry enclosed within the casing, which at least partly comprises a controller, such as a microprocessor or the like, and which provides control signals to control the output or outputs of at least the blower unit 7, and preferably other items such as the humidifier chamber 12. The control circuitry also can be adapted to receive signals from sensors in the system (e.g., pressure, flow, humidity and temperature signals from these sensors as applicable) and to alter outputs from the control circuitry accordingly. In some cases, the gases modification unit (e.g., the blower unit 7) includes a gases path that extends between an inlet to an outer casing of the gases modification unit and an outlet port that is configured for connection to a gases conduit in use. The gases modification unit can be configured to use a sensor 99 and/or other sensors to establish that a conduit is correctly connected to the outlet port of the gases modification unit by confirming that at least one stored value correlates with one or more of (i) air flow through the gases path and (ii) air pressure within the gases path. The control circuitry also receives signals from user controls as the user controls are manipulated by a user and alters the output signals accordingly.

Active Status Indicator

As outlined above, one of the major design considerations when designing and manufacturing domestic breathing assistance systems is a desire to minimise operating noise as much as practically possible. However, effective noise reduction can lead to some unforeseen secondary difficulties. If the noise reduction is too efficient, it can be difficult for a user to establish whether or not the apparatus is operating (i.e., producing a gases stream suitable for therapy). Software or control routines can be included that can. gradually increase, or ramp up, the operating flow or pressure from an initial start mode (i.e., low pressure and low flow) to a full operating mode (i.e., higher pressure and higher flow). Ramp modes or the like allow a user to fall asleep before they experience full gases pressure and flow, which can be irritating to a user who is awake and which can reduce the ability of a user to easily fall asleep. As a user falls asleep, the pressure and flow increase gradually (i.e., "ramp up") to full operating conditions. However, when using these type of "gradual start" or "rampup" routines, it is possible that a user can fall asleep thinking that the machine is active but not yet in a full operating mode (i.e., the machine will ramp up once they are asleep) when the machine is actually inactive or in a standby mode. This can be inconvenient because a user will not receive the desired therapy and may not receive adequate fresh gases.

Even if "ramp up" routines are not used, it is possible for a user fall asleep assuming that a machine is running when it is actually inactive and thus not receive the desired therapy. With a machine that has been designed to have effective noise reduction, there is little aural reminder of the operating status. The system can be on, but not running in an operating mode, and so a user can inadvertently think that the system is operating.

In embodiments of the present invention, this problem is solved by including a display that visually indicates the operating or function condition, or that includes an indicator as part of the main user display. If the unit is in an operating mode (i.e., a mode in which it actively is, or shortly will be, providing flow and pressure for therapy), then the visual indicator is active. If, in contrast, the unit is off or in a standby mode where pressure and flow at therapeutic levels will not be provided unless the situation changes, then the visual indicator is inactive. In some embodiments, the user display 9 includes or incorporates the visual indicator that shows whether or not the system is in an operating mode. In some embodiments, the visual indicator could be separate from the main display 9; however, the presently illustrated configuration includes the visual operational indicator as part of the main LCD display 9.

According to some embodiments, the assisted breathing unit 6 has a plurality of operating modes. For example, the unit 6 may provide a CPAP mode with a delayed start, a CPAP mode with an initial pressure ramp and an automatically titrating mode that manages the therapeutic pressure in response to sleep disordered breathing events.

Preferably, the controller activates the same visual indicator in respect of all modes in which therapy is being, or will be, supplied. For example, the controller activates the visual indicator when any of the CPAP operating modes is active but leaves the visual indicator inactive when the unit is in a standby mode.

Removable Peripheral Device Connection Display

In some embodiments, the breathing assistance apparatus also is adapted to allow the attachment of a removable peripheral device or a removable memory device 10 that can have a read-writable memory and an integral connector 11. In some embodiments, the removable memory device 10 is a Universal Serial Bus (USB) memory stick type of electronic storage device. Alternatively, the removable peripheral device may be any type of removable or portable (e.g., pocket-sized or the like) electronic storage device, such as a smart card. The removable memory device 10 may also include embedded integrated circuits that can process information and store data.

The integral connector 11 of the removable peripheral device 10 is adapted for removable connection to the blower unit 7 via a slot or port 13 on the casing of the blower unit 7. An electrical communication pathway is formed when the peripheral device 10 is connected to the port 13 on the blower unit 7 or another portion of the assisted breathing unit 6. Once the connection is made, data can be uploaded to or downloaded from the removable memory device 10 to the controller of the assisted breathing unit 6, which in the preferred embodiment is inside the casing of the blower unit 7.

As has been outlined above, one problem with removable devices of this type is that they can easily be connected improperly, or they can easily become at least partly disconnected during use. This improper connection, incomplete connection or disconnection can occur in a manner that is not easily or immediately apparent to a user at first glance. In other words, the improper connection, incomplete connection or disconnection is not immediately or easily visually apparent.

Certain features, aspects and advantages of the present invention overcome this problem by having a connection display that is adapted to indicate to a user that the removable peripheral device 10 is correctly connected.

In some embodiments, the user display 9 includes or incorporates the visual indicator which shows whether or not the removable peripheral device 10 is correctly connected to the port 13. That is, the connection display is incorporated as part of the main display 9, with the controller activating part of the display to show that the removable peripheral device 10 is correctly connected to the port 13 and to visually indicate to a user that the connection has been correctly established.

In alternate embodiments, this visual display could be separate from the main display 9. For example, the visual display could be an LED 14 offset from or positioned proximate the port 13. When the removable peripheral device 10 is correctly connected, the LED 14 will energise or light up to indicate to a user that the removable peripheral device 10 is correctly connected to the port 13.

There are many ways by which this can be achieved. For example, the integral controller in the blower unit 7 can interrogate the removable peripheral device 10 and establish if it is correctly connected or not. Once the controller has established that the removable peripheral device 10 is correctly connected, the controller can energise the relevant portion of the display or the LED 14.

In a further alternative embodiment, the connection display does not have to be electronic, but could be a line, a ridge or other physical visual display indicator on the removable memory device 10 that aligns with the edges of the slot defining the port 13 to show a user that the removable peripheral device 10 is correctly connected.

In a yet still further embodiment, the integral controller is not required to carry out any actions to establish if the connection has been made. Rather, correct insertion of the removable peripheral device 10 into the port 13 could close a switch or otherwise complete an electrical circuit or the like which would not be closed or completed unless it was correctly inserted, and which is isolated from, or otherwise independent of, the main controller. Completing the electrical circuit activates or energises the visual display (e.g. the display or the LED 14).

Conduit Connection Display

As outlined above, incorrect connection or reconnection of the conduit or hose 21 to the gases source via connector 25 can cause breathing gas leaks. Incorrect connection can also mean that the desired electrical contact between the static gases source (e.g., the blower unit 7 in the preferred embodiment) and the electrical elements in the conduit 21 can be intermittent or non-existent. Certain features, aspects and advantages of the apparatus of the present invention solves this problem by including a conduit connection display as part of the apparatus. In the most preferred embodiment, the LCD user display 9 includes or incorporates the visual indicator that shows whether or not the conduit 21 is correctly connected. In other words, the conduit connection display can be incorporated as part of the main display 9 with the controller activating part of the display to show that the conduit 21 is correctly connected and to visually indicate to a user that the connection has been correctly established.

In an alternative form, the conduit connection display could be a separate LED 15 located at or close to the patient outlet 25.

For example, the controller can establish that the connection between the patient outlet 25 and the conduit 21 has been correctly made by sending an interrogation signal or like and then visually indicate to a user (e.g., energize the relevant portion of the LCD display 9 and/or the LED 15) that the connection has been correctly made.

There are many ways in which the controller may establish that the connection has been correctly made: by sending an interrogation signal, by receiving signals (e.g., from sensor 99) indicative of current flow, air flow or pneumatic pressure and comparing these to stored values, or by receiving a signal that could not be sent unless a physical connection had been made correctly within the patient outlet 25 and the conduit 21 (e.g., correctly connecting the two items could close a switch or make the final connection in a dedicated electrical pathway).

In a yet still further embodiments, the integral controller is not required to carry out any actions to establish if the connection has been made. For example, correct connection of the conduit 21 to the connector 25 could close a switch or otherwise complete an electrical circuit or the like, which is independent of the controller. Completing the electrical circuit either directly or indirectly activates or energises the relevant portion of the display 9 or the LED 15.

Control Menu Functionality

In the preferred embodiment, the control menu is displayed on the display 9. In the preferred embodiment, the display 9 is an LCD display. The illustrated display 9 provides a circular ring of options adjacent the outer edge of the display 9. As the knob 8 is rotated, each of the options will activate in turn. When the knob or other selection button is depressed by the user, the activated option will be chosen.

Once an option or parameter is chosen, for example "output power", the level of this option or parameter can be adjusted by rotating the knob 8 clockwise and anticlockwise. A user can then exit this submenu and return to the main menu by, for example, tapping the knob inwards or pulling it outwards. The control circuitry can be programmed as required. Other options can be pre-programmed as desired. For example, pushing and holding in the knob 8 (or pulling it outwards and holding it out) could turn the unit off.

It is preferred that the mechanism of the knob 8 has a series of physically discrete positions and that the knob requires a small force to move between these positions. Preferably, the discrete positions (the "cogging" positions) that the knob 8 reaches as it is rotated correspond to different menu option positions.

The user interface functionality can be implemented by the controller. For example, the controller can include a stored control program and parameter data. The parameter data can include data indicating the accessibility status of each of the options. As will be discussed below, the controller activates the display icon of each of the accessible options. According to the control program, the controller may cause a predetermined icon from the displayed icons to be initially highlighted. For example the controller may activate an additional display element proximate to the icon. As the controller receives indications of movement of the knob 8 in a direction, the controller selects (as the direction dictates) an adjacent accessible option, removes highlighting from the initial icon and highlights the icon of the next option.

When the controller receives input of a selection button press, the control program responds by calling a routine associated with the option presently active and highlighted. This routine may invoke further layers of menu functionality, or may provide for setting a usage parameter. Preferably, the routine will display information and options for amending or changing the information.

As has been outlined above, breathing assistance apparatuses are getting more complex and sophisticated and the number of control options has increased. An end user does not require a high level of control sophistication and can easily become confused or overloaded if presented with too many options for adjusting or controlling the output. Too many options can also be counter-productive if a user does not entirely understand the implications of changing the control parameters. However, a health professional may require a greater degree of control input when making adjustments to the operating conditions than is desired byan end user.

In order to overcome this problem, certain features, aspects and advantages of the preferred embodiment of the device of the present invention includes a, way of removing access to a variable amount of the control functionality. A clinician or other health professional will have access to the full spectrum of functionality but can set the user interface so that an end-user (i.e., a person who receives therapy from the system) will initially be able to access a certain amount of control functionality, and will be locked out or otherwise unable to access some of the more sophisticated control elements or control subroutines. The user interface is adapted to display a control menu that has a number of control and display options. The controller has control options that are able to be manipulated to hide or block at least one, and preferably a plurality, of the control and display options. Once hidden, the control options are able to be manipulated to unhide or unblock the control and display options. In contrast, a health professional will be able to access those elements that are denied to the end user, by unlocking another level of the interface in order to access a greater range of functionality.

For example, a routine of the control program may include program code for presenting on the screen options for amendment of the accessibility parameter data. In response to user input using the knob and button, the controller may then adjust the stored parameter data.

Alternatively, the control program may update stored parameter data using data received over an external communication interface, or uploaded from a portable memory device.

If appropriate, once a user becomes more familiar with their own apparatus, they can be given access to some or all of this extra functionality. The control system is configured so that it is possible to gradually unlock more and more of the functionality, or to lock out or unlock various different individual functions or combinations of individual functions. This can be achieved by using a keying mechanism (electronic or otherwise), a password-protection routine, or any of a number of similar mechanisms or methods that are known in the art.

For example, the routine of the control program intended for amending the accessibility settings may include steps for displaying a prompt for password input, receiving input data in the form of a sequence of knob rotations, button pressures, or both, and check the input sequence against stored comparison data. Alternatively, the routine may prompt the user by sound or display, for example, to identify themselves using a biometric sensor on the unit or by inserting a personalised data storage device. Embodiments of the control functionality will now be described with reference to FIG. 5.

In the illustrated embodiment, the user display 9 is capable of displaying a number of symbols and menu options relating to the control and output of the blower unit 7, for example. The controller can be initially set so that the totality of these menu functionality symbols and icons can be viewed, as shown in FIG. 5*e* (e.g., a "clinician mode"). More limited menu options are shown in FIGS. 5*a-d*, where various combinations of the icons and symbols are hidden or "blanked out", and are unavailable. One or more of these menus can be selected and made available to a user. For example, in some embodiments, the menu options shown in FIGS. 5*c* and 5*e* can be blocked while those shown in FIGS. 5*a*, 5*b*, and 5*d* remain available to be selected as desired. Alternatively, access to the most basic of menu functions and display, as shown in FIG. 5*a*, initially can be provided and, over time and with experience, greater functionality can be unlocked. For example, a clinician can, after a certain period of time, unlock the second menu as shown in FIG. 5*b* to allow a user access to the greater functionality. Then, after a certain time, a yet more complex menu/display as shown in FIG. 5*d* can be unlocked. The clinician can also "re-lock" the menu functions as desired. In some embodiments, the controls are configured so that all possible combinations of menu functionality are available.

The controller may include functionality to effectively disable the user input controls according to certain conditions. In particular, the controller may disable the effect of the user input controls after a period of non-use of the controls. The control program may implement this functionality in any suitable way.

For example, the control program may set (or reset) a response timer each time a user control is activated, and steadily reduce the value of the timer. When user input is sensed, the program may check the response timer and either respond to the sensed input if the timer is above zero or, if the timer has expired, respond to the sensed input by implementing an activation test. The activation test may include displaying a prompt requesting specific manipulation of the controls to activate the user interface. The program monitors for sensed inputs corresponding with the specified manipulations. For example, the specified manipulation may be depressing the button for a predetermined period, depressing the button a predetermined number of times, or performing a sequence of rotations of the knob. If the program receives data indicating manipulations that match the requested sequence, the program resets the timer so that subsequent user input is not blocked. Otherwise, the controller ignores the user input. The program may start or reset an additional short timer at each sensed user input during the test, and exit the test mode if the short timer expires.

By way of example, user input may be disabled after an inactive period preset to a value between 5 and 10 minutes and user input may be enabled by depressing the button for 3 seconds.

The intention of disabling user input is to reduce the likelihood that the device will be easily disrupted during operating modes because of, for example, the dark bedroom environment in which the device will usually be used.

As an additional step in deciding whether to act on user input, the control program may respond differently according to other operations of the device. For example, the control program may only disable input during an operating mode, and not when in standby mode. In some configurations, the control program may have certain modes where it will respond to some or all user input. For example, the control program may respond to input when the controller also is sounding an alarm. Such a configuration ensures that a user does not need to complete the activation test merely to deactivate the alarm.

Power Conservation Mode

The improved form of breathing assistance apparatus is adapted to be capable of connection to an external power supply. In some embodiments, the blower unit 7 has a socket to allow the unit to be connected to a source of mains power (e.g., either by plugging a power lead into the unit or via its own integral built-in lead). In normal operating mode, breathing assistance systems can use a large amount of power over an extended period (e.g., when running at full power for a full eight-hour sleep period). This is not normally an issue if the system is connected to a source of mains power. However, there are occasions when a user may not have access to a mains power supply. For example, if the user is travelling then they may not be able to connect their system to a mains power source. The user could be on a long-haul flight. Alternatively, the user could, for example, be a trucker, fisherman or member of a similar group who regularly sleep in their vehicles.

Certain features, aspects and advantages of the preferred embodiment of the present invention therefore have the control program capable of causing the controller to provide a power conservation or power saving mode, which is user-selectable or which the apparatus automatically switches to if the controller senses that it is running on a supply other than a mains power supply. Thus, the control program can automatically switch from a standard or full-power mode to a power saving mode. Alternatively, if the power-saving mode is intended to be user-selectable, the control program may allow the user to manually select the power saving mode via the user interface. In some embodiments of the power saving mode, the controller limits work done at a maximum rate of between 50 and 100 Watts, or at about 75 Watts. However, in alternative embodiments, the control program may allow a user to set the maximum rate, or the rate could be pre-programmed at a different maximum. The control program may allow a user to switch back to full power mode when the unit is connected to a mains power supply, or the controller may be programmed to automatically switch back to a full power mode once reconnected to a source of mains power. Alternatively, the control program may allow a user to manually override the power saving mode and switch to the full-power mode when the unit is not connected to a mains source, if desired.

There are several ways in which the control program may detect whether it is connected to a non-standard or non-mains source of power. Several ways in which the system can detect this are outlined below.

Firstly, as has been outlined above, a user may plug their system into the electrical circuit of an aircraft. Typically, a normal mains circuit will operate at a certain frequency—for example, in the USA, the mains circuit is AC and operates at 60 Hz. In Europe, and many other countries, the AC mains circuit operates at 50 Hz. An aircraft's electrical circuit will for example, run an electrical system at 400 Hz rather than 60 Hz. The advantage of this is that the power supplies are smaller and lighter, a prime consideration in aircraft design. An electrical system of this type, capable of powering devices usually powered by mains power can be generally referred to as providing a synthesised mains AC power supply. When a user plugs their breathing assistance system into the aircraft's electrical system, the electrical circuitry in the system will receive power at a frequency of 400 Hz. In one embodiment, the electronic circuitry of the system is adapted to detect the frequency of the power supply. If the power supply is delivered at a "mains" frequency (e.g. 50 Hz for Europe, 60 Hz for the US, etc), then the electronic circuitry operates the system in a standard mode, and the system is powered as normal. If the electronic circuitry detects that the frequency of the power supply is outside this pre-set range, then the controller will switch the system to the power-saving mode.

In a vehicle such as a truck, the electric circuit is usually battery-powered and is usually a 12V or 24V DC supply. A mains-type socket may be provided in the circuit to allow a user to plug mains-enabled devices into the circuit to draw power from the vehicles power supply. Usually, an inverter will be fitted in the circuit to convert the DC current of the vehicle circuit to AC so that AC devices can be powered. Power provided in this manner can generally be referred to as a synthesised mains AC power supply.

In some embodiments of the breathing assistance system, the system can be fitted with a detector that receives a signal indicating that it should switch from the normal mode to the power-saving mode. For example, the system can be fitted with an infra-red detector or a Bluetooth detector, for example, connected to the electronic circuitry. On receiving a signal indicating that synthesised mains AC power is being provided, rather than "true" mains power, the system will switch to the power-saving mode. Alternatively, a secondary signal can be superimposed over the power supply signal, the secondary signal detected by the electronic circuitry of the breathing assistance system, and the circuitry switching the system to the power-saving mode on detection of the superimposed signal.

Alternatively, the system can be fitted with user controls that are adapted to allow a user to manually switch between a standard operating mode and a power saving mode.

The controller in alternative forms could also be powered by an internal power source or batteries. The system could switch automatically to a power-saving mode when disconnected from a main power supply, or this could be carried out manually by a user using the user controls.

As shown in FIG. 3, and described above, the blower unit 7 has the patient outlet 25 passing out of the rear wall of the integrated unit 6. As described above, the patient outlet 25 is adapted to allow both pneumatic and electrical connection to one end of a conduit (e.g., the conduit 21) running between the unit 6 and the patient interface (e.g., the interface 4). In some embodiments, an integrated unit (or modular unit) that includes an improved form of elbow has two advantages over the prior art. Firstly, the elbow is removable from the rest of the blower unit 7 for cleaning, maintenance, or the like. Secondly, the elbow is structured in such a manner that gases flowing through it are insulated. Thus, the heated humidified gases passing out of the blower unit tend to lose less heat to the atmosphere or ambient surroundings than would otherwise be the case. Embodiments of an elbow connector that embodies these two advantages will now be described with reference to FIGS. 6, 7, 8 and 9. It should be noted that these two advantages do not have to be simultaneously realized, and that each could be realized separately from the other.

Removable Elbow Connector

Figure 6:
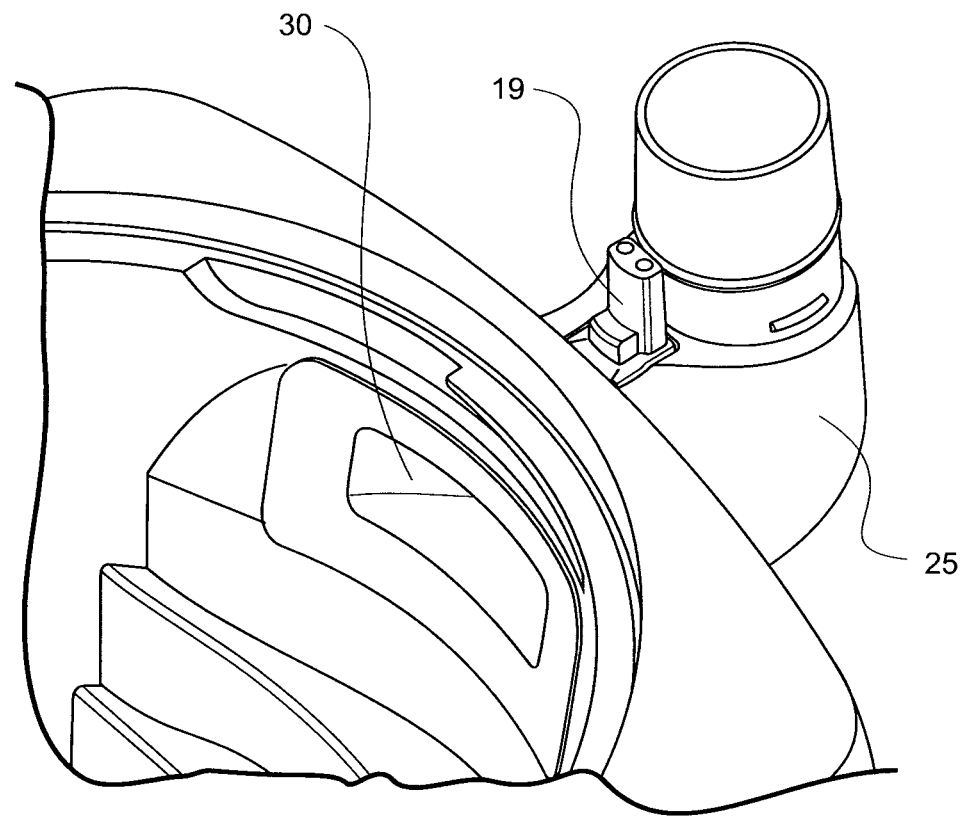
FIG. 6 shows a rear view of the blower unit with the humidifier removed to show a removable seal that forms a passage to a patient outlet or elbow, which passage extends through a rear wall and an outer casing of the blower unit.

A close-up of the blower unit 7 is shown in FIG. 6, looking from above and to the rear, from one side. The enclosure 42 for the humidifier unit 31 is shown with the humidifier unit 31 removed from the blower unit 7.

In use, the outlet of the humidifier chamber 31 connects with the inlet aperture 30 of a removable seal 32. The removable seal 32 forms an outlet gases passage such that heated humidified gases from the humidifier chamber 31 can pass into the patient outlet 25 and on to the patient 1. In some embodiments, at least the inlet aperture 30 of the removable seal 32 is formed from a soft sealing material, such as silicone rubber, for example but without limitation. The structure and composition of the removable seal will be described in greater detail below.

Figure 7:
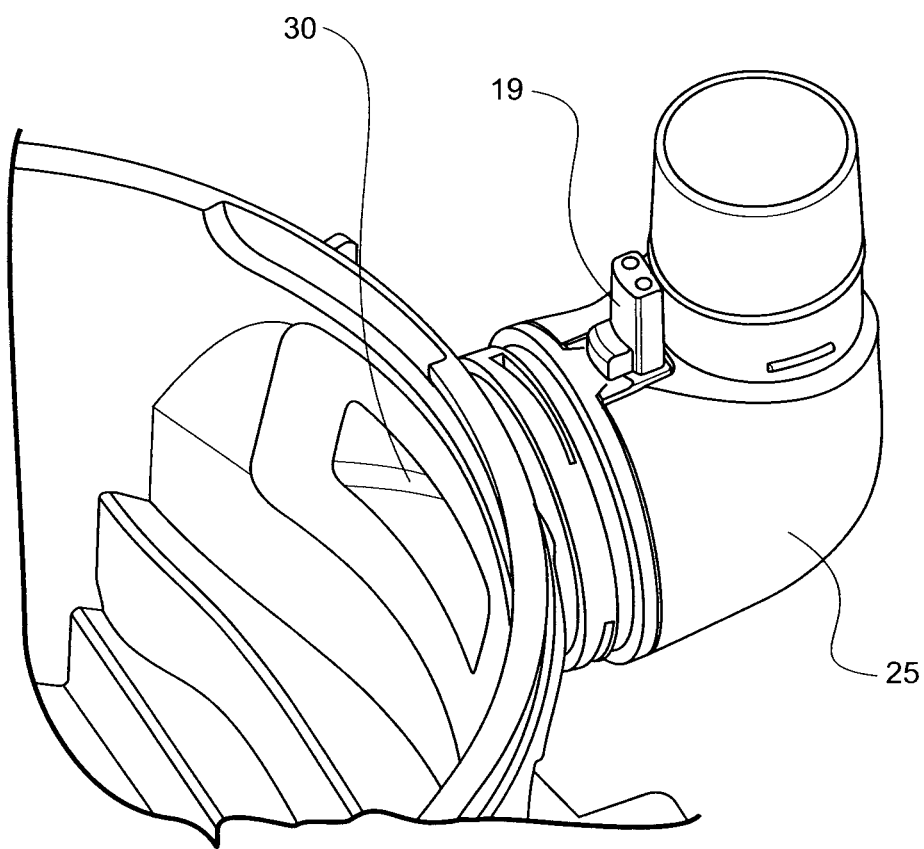
FIG. 7 shows the same view as FIG. 6 with the outer casing removed.

FIG. 7 shows further detail of the connection between the patient outlet or elbow 25 and the rest of the blower unit 7. For clarity, the outermost casing of the blower unit is not shown. The path between the inlet aperture 30 and the elbow connector 25 can be seen.

Figure 8:
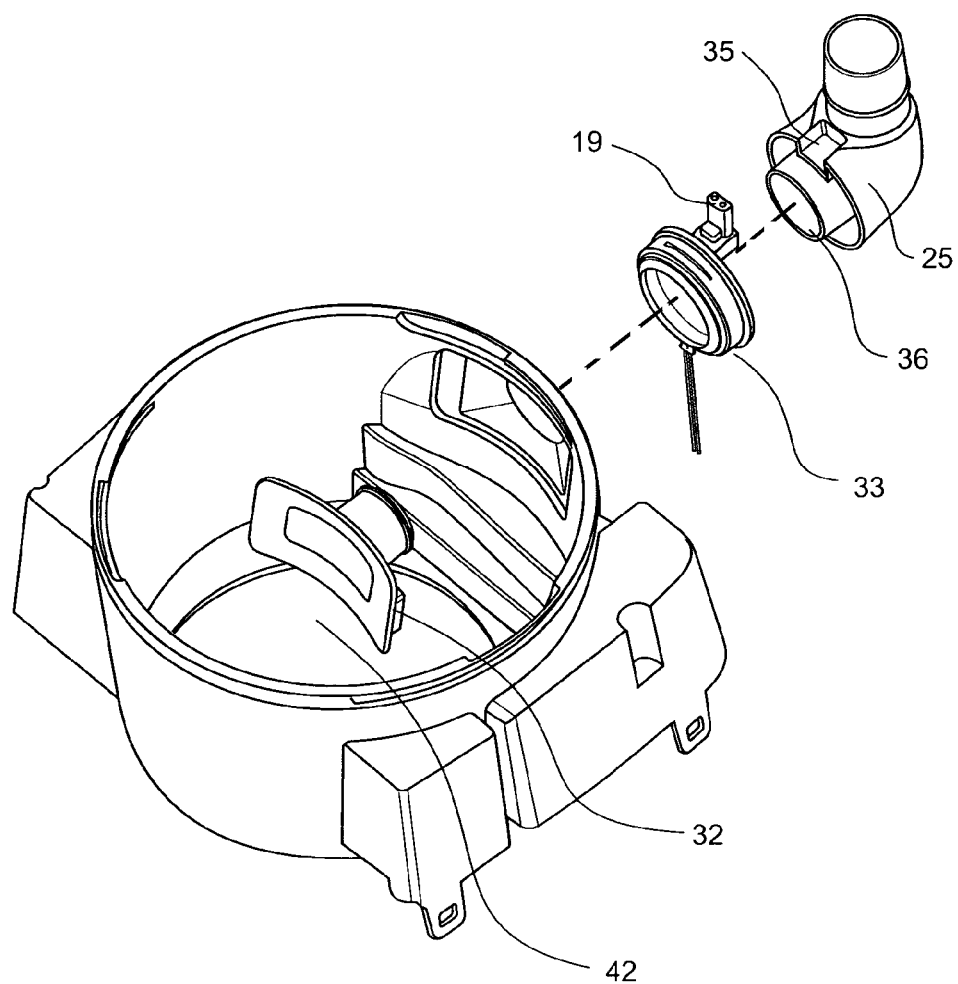
FIG. 8 shows an exploded view of the portion of the blower unit that forms the enclosure with the removable seal, the patient outlet and a sealing/connection ring that fits on and around part of the patient outlet shown.

FIG. 8 shows an exploded view of those parts of the blower unit shown in FIG. 7. The enclosure 42 for the humidifier chamber 31 is shown. Also shown are the patient connector 25, the removable seal 32, and a sealing/connection ring 33 that rigidly connects to the inner end of the patient connector or elbow 25. Preferably, when connected together, the sealing ring 33 and the elbow 25 cannot move relative to one another.

The structure of the illustrated elbow 25 now will be described with particular reference to FIG. 10. The illustrated elbow connector 25 is formed so that it has substantially a right-angle or 90-degree bend at the centre, which divides the elbow 25 into two halves or portions of substantially equal length. An inner portion closest to the blower unit is adapted to connect to the blower unit 7 in use. An outer portion in use connects to the patient conduit 21. The inner end 36 of the inner portion of the elbow 25 is formed as a gases inlet so that in use it can receive gases from the humidifier 31. The outer portion connects to the inner end of the conduit 21 in use.

The illustrated sealing ring 33 is formed as a rigid ring that fits over and around the inner end 36 of the elbow 25. The inner end 36 has a pair of indents or slots 47 formed on the outer surface thereof, with a pair of complimentary ridges 48 formed on the inside surface of the sealing ring 33. These allow the sealing ring 33 and the elbow connector 25 to clip or slot together via friction fit, for example. In other words, the ridges 48 may fit into the slots 47 to hold the two parts together.

The illustrated sealing ring 33 also includes an electrical connector 19. The electrical connector 19 preferably fits into an indent or recess 35 in the elbow 25. The recess 35 can be formed on or at the inside corner of the elbow 25. The electrical connector preferably is aligned so that when the sealing ring 33 and the elbow 25 are connected, the electrical connector 19 is generally parallel with the outer portion or half of the elbow 25. This allows electrical and pneumatic connection between the elbow 25 and a connector on the end of conduit 21 to be achieved easily in one action.

In use, the illustrated sealing ring 33 is fitted into the outer casing of the blower unit 7 and is generally non-removably held in position therein. For example, a circlip or similar engaging mechanism may be interposed between the casing and a flange of the sealing ring. Such a configuration can best be seen by comparison of FIGS. 6 and 7, with FIG. 6 showing the outer casing and FIG. 7 showing a similar view with the outer casing not shown. Because the elbow 25 is held in place by a friction fit with the sealing ring 33, for example, the elbow 25 can be removed by pulling it outwards away from the blower unit 7. This allows the elbow 25 to be easily removed for cleaning or replacement as desired.

Insulated Elbow Connector

One well-known problem with the provision of heated, humidified gases to a user from a CPAP-style system is that the blower and humidifier components of the system tend to be located at a distance from the point of delivery. There is therefore some difficulty in maintaining the temperature of the gases between the blower/humidifier part of the system and the point of delivery. In the art, this is mainly addressed by heating the conduit 21 to maintain the temperature. However, it remains desirable to minimise as far as possible all potential ways in which heat can escape from the gases.

In accordance with certain features, aspects and advantages of the preferred embodiment of the present invention, gases exiting the humidifier unit 31 enter the removable seal 32 and then pass into the elbow 25. The outer end of the removable seal 32 is located inside the inner end of the elbow 25 such that there is some overlap between the two.

Figure 9:
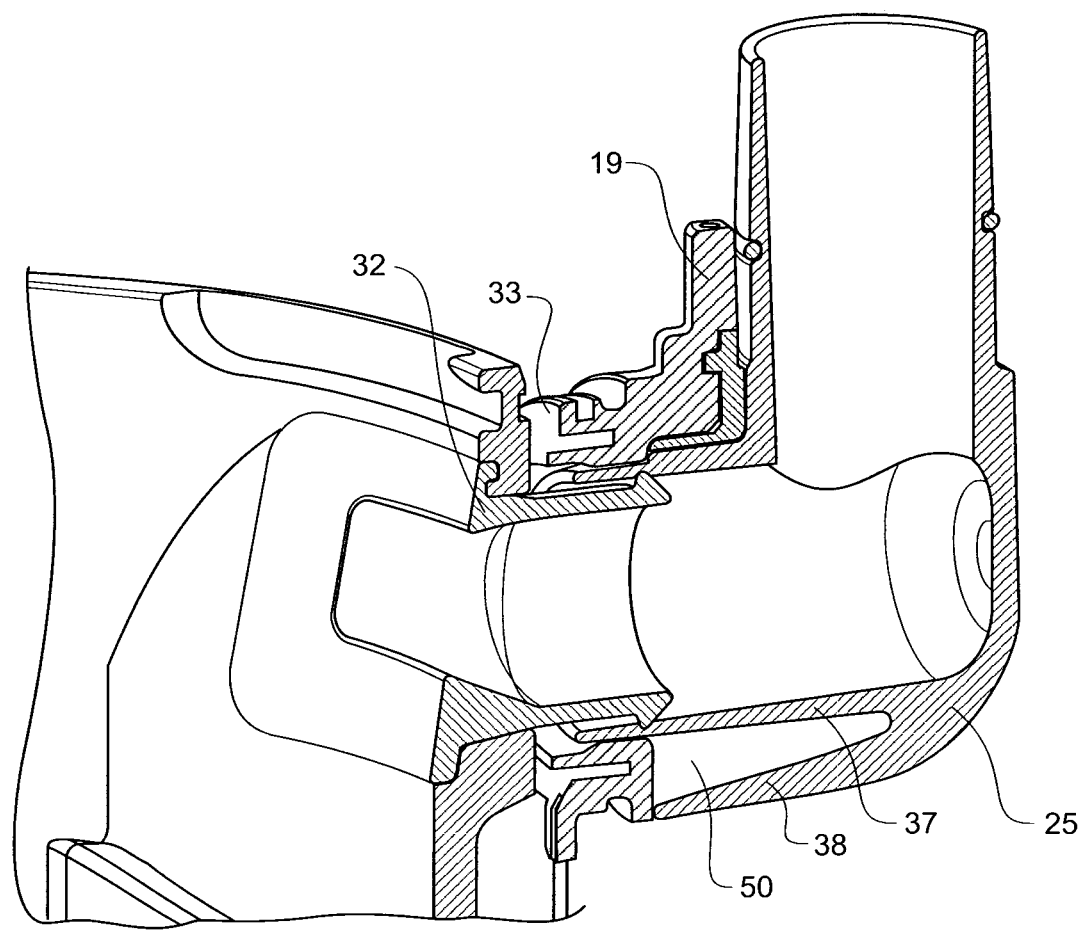
FIG. 9 shows a cutaway view of the rear of the blower unit with detail of the removable seal, the sealing/connection ring, and the elbow connector or patient outlet also shown.

FIG. 9 shows a cross-section of the seal 32, the blower unit 7, the sealing ring 33 and the elbow 25. As can be seen, the outer end of the seal 32 passes into the inner end of the elbow 25, and there is overlap between the two. Gases travelling through the innermost portion of the elbow 25 are insulated from atmosphere because they are surrounded by the removable seal 32, the inner portion of the elbow 25, and the sealing ring 33. The outer arm or outer portion of the elbow 25 is in use surrounded by the connector portion 34 of the conduit 21, as can best be seen in FIG. 3. This effectively insulates the gases in the outer arm of the elbow 25.

Figure 10B:
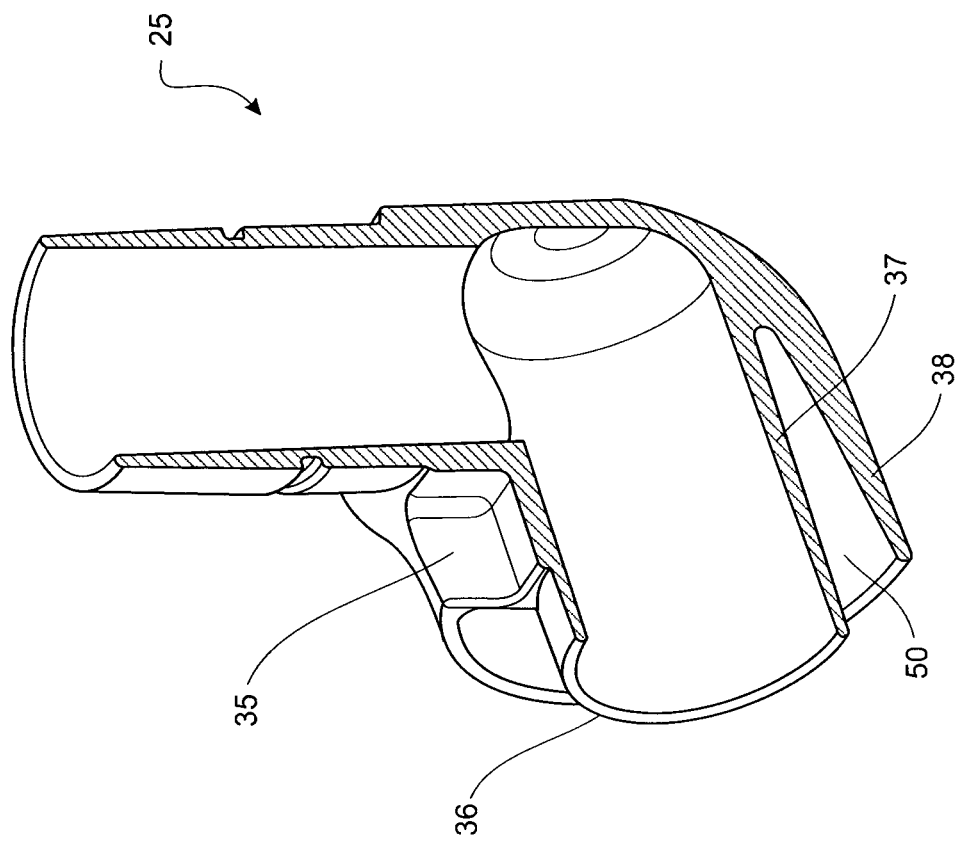
FIGS. 10a and 10b show detail of the patient outlet.
Figure 10A:
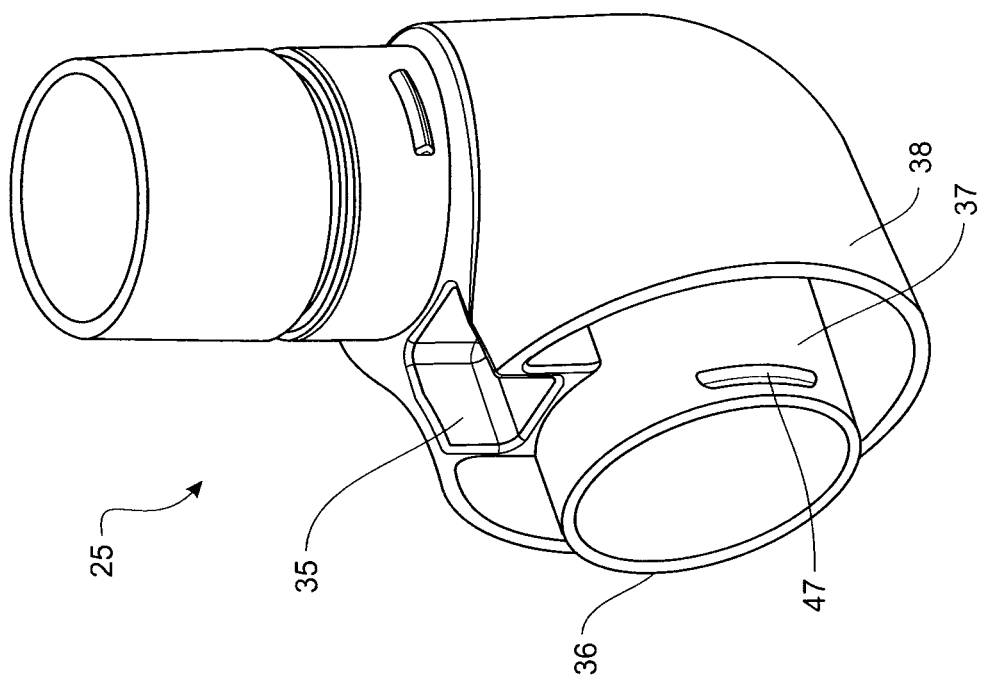

With reference to FIGS. 9 and 10, the remainder of the elbow 25, the outer portion of the inner arm, is insulated by surrounding an inward gases passage 37 with an insulating wall 38, spaced from the inward gases passage 37 so that an airgap 50 is formed between the passage 37 and the wall 38. In use, this airgap 50 is closed to the atmosphere on its open side (i.e., the inner or blower side) by the sealing ring 33.

In this embodiment, the air gap 50 completely surrounds the inward gases passage 37, except for the recess 35. The recess 35 has the effect of causing the insulating wall 38 to curve inwards to contact the passage 37, as best seen with reference to FIG. 10a.

The air gap 50 between the inward gases passage 37 and the insulating wall 38 serves to insulate the gases flowing through the elbow 25 and assists in retaining the heat of these gases.

Removable Seal

Figure 11A:
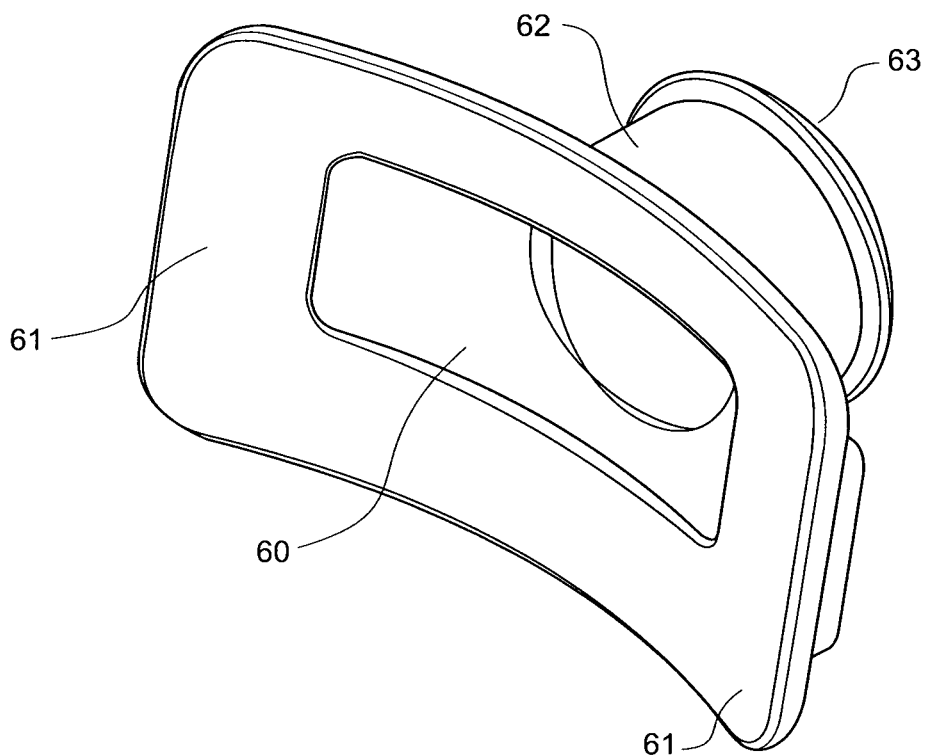
FIGS. 11a and 11b show detail of the removable seal.
Figure 11B:
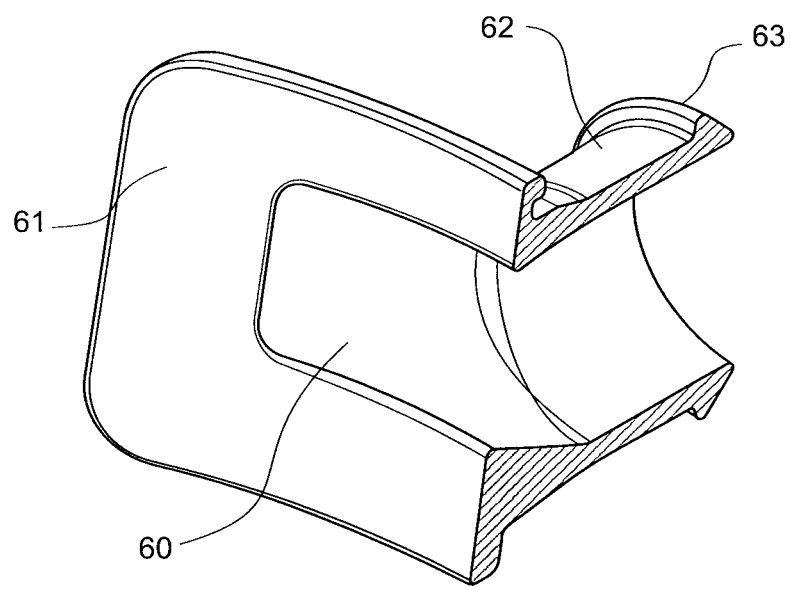
Figure 12:
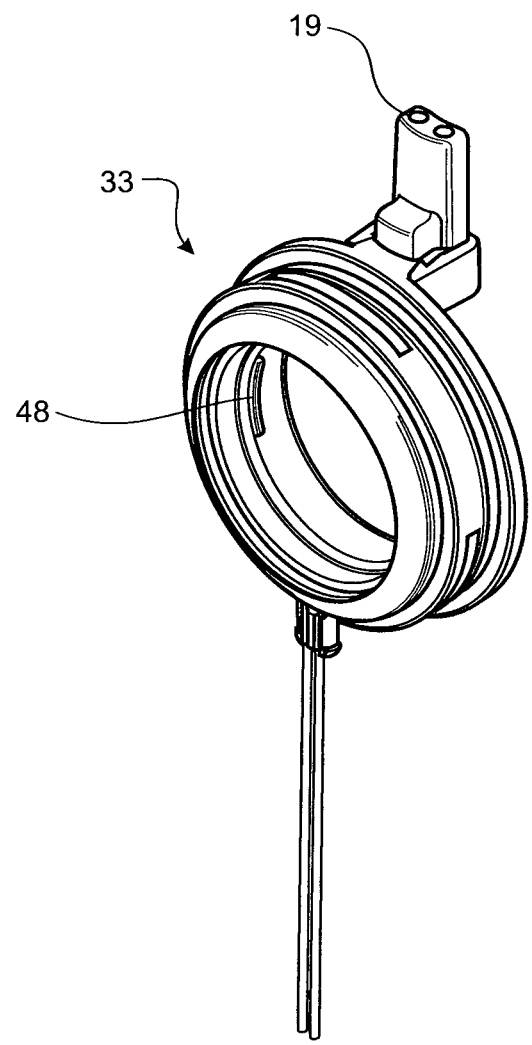
FIG. 12 shows detail of the sealing/connection ring.

The removable seal 32 will now be described with particular reference to FIGS. 9 and 11. As described above, the outlet of the humidifier chamber 31 connects with the inlet aperture 30 of the removable seal 32 so that heated humidified gases from the humidifier chamber can pass through the removable seal 32, into the patient outlet 25 and then on to the patient 1. The removable seal 32 forms an outlet gases passage for the blower unit. In some embodiments, the entirety of the removable seal 32 is formed from a soft, flexible material, such as silicone rubber, for example but without limitation. With reference to FIG. 11a, the overall form of the illustrated seal 32 is that of a funnel. The inner portion of the seal 32 forms a wider mouth 60 of the funnel.

The opening of the mouth 60 (i.e., on the inner side) is substantially rectangular such that the mouth portion of the funnel has the shape of a rectangular funnel. The opening of the illustrated mouth 60 is surrounded by a flange 61 that in use seals against the side surface of the rear wall of the enclosure 42.

The flange 61 can, if desired, include ridges or the like (not shown) that press-fit into complimentary sockets or slots in the blower unit to hold the removable seal 32 in position. In some embodiments, the flange 61 and at least part of the mouth 60 are curved so as to fit flush against the curved rear wall of the enclosure 42.

The outer portion of the illustrated removable seal 32 forms a stem 62 of the funnel. The outermost end of the stem 62 has a rim 63 that is wider than the remainder of the stem 62. The rim 63 is shaped so that the stem 62 and the rim 63 has a barbed appearance in cross-section with the rim 63 being wider at the inner side than at the outer side.

In use, to assemble the illustrated blower unit, the removable seal 32 is pressed into and through an aperture in the rear wall of the blower unit to form an outlet passage from the humidifier chamber outlet, through the wall of the blower, and into the elbow 25. The illustrated rim 63 has an interference fit with the inner surface of the inward gases passage 37 of the elbow such that a seal is formed between the two.

The removable seal 32 can be removed from the blower easily, such as by pulling it out of the wall of the blower unit. This is useful for cleaning, maintenance or replacement. The interference fit between the stem 63 and the inner arm of the elbow 25 provides a gas-tight seal between the two components. The elbow 25 may still be rotated relative to the removable seal (i.e., the rotation taking place around an axis that substantially forms the centre line of the stem 62).

Humidifier Chamber

The humidifier unit 31 will now be described in more detail with reference to FIGS. 13-17.

In some embodiments, the humidifier unit 31 is comprised of three main parts: a humidifier chamber 112, a lid 132 and a locking handle 122, which is counted as part of the humidifier unit for the purpose of describing the operation of the integrated unit 6.

In some embodiments, the humidifier chamber 112 is an open-topped container with a heat conducting base. The illustrated chamber 112 is sized to fit snugly within the enclosure 42 on the integrated unit 6. In other words, the chamber 112 is enclosed within the blower unit except for the open top of the chamber 112. A fully open topped chamber 112 can be provided. However, an alternative form of the chamber 112 could have a closed top surface, and would include an opening on the chamber positioned (e.g., not necessarily on the top surface) and sized appropriately so that a user can easily fill the chamber 112. This opening could be one of the apertures that are normally used for gases delivery in use. The chamber 112 with an open top, and the alternative form that includes a fill opening on the top are referred to as "open top", or "top openings" within this specification. The open top may also be referred to as a "top fill aperture". It should also be noted that when the humidifier chamber 112 is referred to as "enclosed", or "substantially enclosed" in relation to the integrated breathing assistance apparatus, this has the meanings consistent with the construction defined above.

In some embodiments, the chamber 112 is a generally circular cylinder, but the lower part of the rear (relative to the integrated unit 6) is flattened and indented to correspond to ledge 133 on the lower rear side of the enclosure 42. This assists the chamber 112 to be oriented correctly in use. It should be understood that other methods of achieving the same result could also be used. For example, the chamber 112 and integrated unit 6 could include complimentary grooves and slots or the chamber 112 could be non-cylindrical so that it only fits the housing in one orientation.

The chamber 112 can also include features such as a fill or level line.

A humidifier inlet port 115 and a humidifier outlet port 116 can be located in the wall of the humidifier chamber 112. In the illustrated configuration, the inlet port 115 and the outlet port 116 are located towards the top of the chamber wall. These are positioned so as to align with a blower inlet port and a blower outlet port when the humidifier chamber 112 is in position. In use, air from the blower unit passes into the humidifier chamber 112 through the humidifier gases inlet port 115, passes through the chamber (becoming heated and humidified as it does so), and exits the humidifier chamber 112 through the humidifier gases outlet port 116 and passes into the passage formed by the removable seal 32. The internal structure of the humidifier chamber shall be described in detail below.

In use, the chamber 112 is positioned (i.e., in the correct orientation) within the enclosure 42. The lid 132 then is placed on top of the chamber 112. The lid 132 is sized so that it will pass through the top opening of the integrated unit 6. A lower surface of the lid 132, close to the edge, seals onto the upper edge of the chamber 112.

The lid 132 is placed in position on the chamber 112 once the chamber 112 has been filled. The locking handle 122 then is positioned above the lid 132. Lugs 127 on the circumference of the locking handle 122 engage with complimentary grooves 126 on the blower unit 7 to lock the lid 132 in position.

The generally cylindrical chamber 112 and round lid 132 have been described, with locking/unlocking of the lid 132 achieved by rotating the separate locking handle 122. However, this is not the only way in which this effect can be achieved. For example, spring loaded clips could be used, with the clips released by a button placed in a convenient location. A hinged lid could also be used, with a clip and complimentary catch located on the lid and the blower unit, to hold the lid closed in use. Alternatively, the chamber lid 132 and the locking handle 122 could be integrated as a single unit.

In some embodiments, the rim or perimeter of the chamber 112 also includes a chamber seal 110, formed from soft silicone or similar. When the chamber 112 is placed in position in the enclosure 42, the chamber seal 110 is pressed against the wall or walls of the enclosure 42 to ensure that the chamber 112 is sealed, so that air entering the chamber from the blower cannot escape to atmosphere. If desired, a substantially unbroken ring of sealing material such as soft silicone can be provided to the wall of the enclosure 42 at or close to the upper rim of the chamber 12; to form a compartment seal (not shown) instead of or as well as the chamber seal 110.

Figure 13:
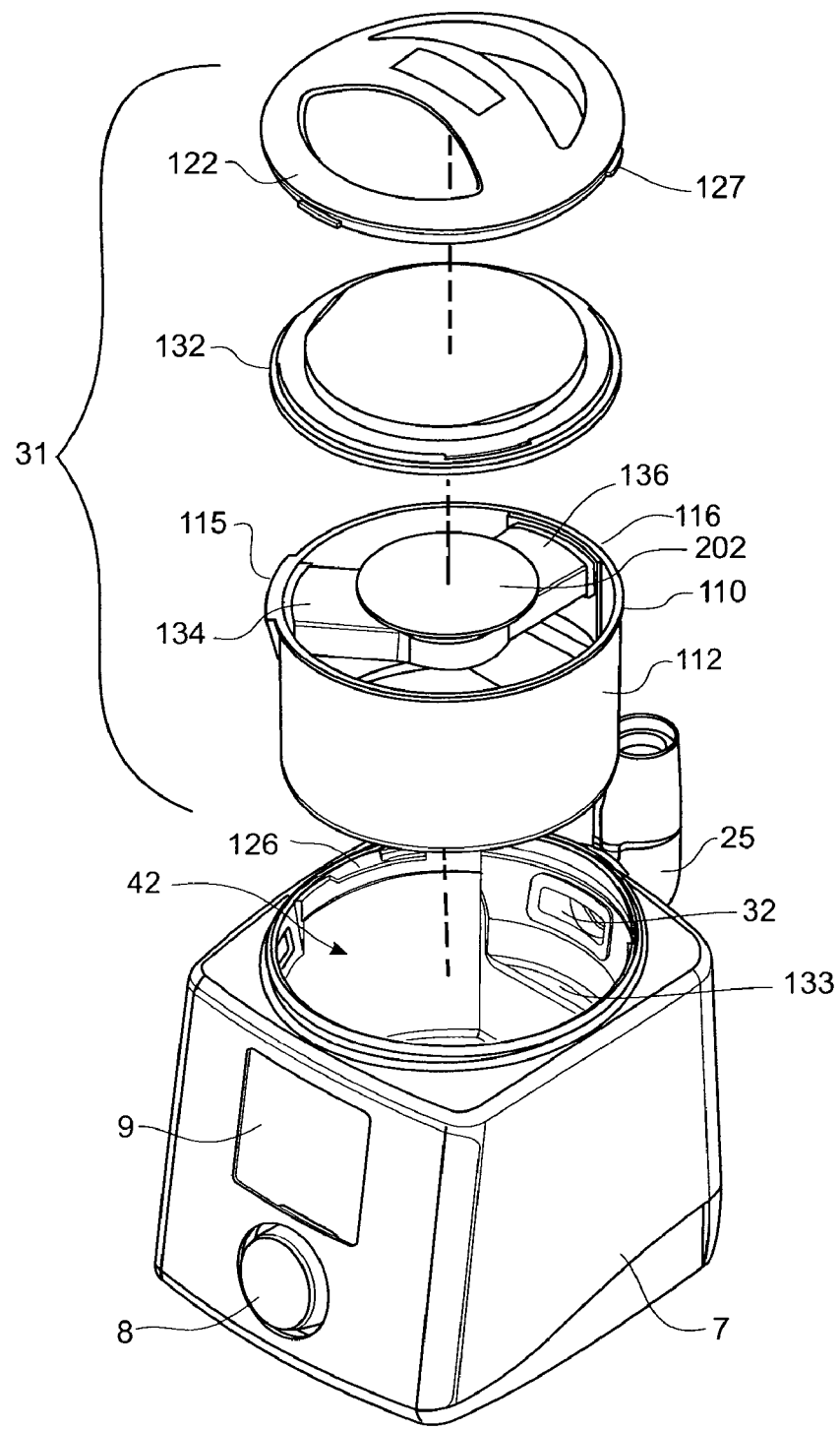
FIG. 13 shows an exploded view of the blower and humidifier unit of the breathing assistance apparatus as shown in FIG. 3, wherein the humidifier unit comprises a humidifier chamber, a separate chamber lid and a separate handle.

As can be seen in FIG. 13, the humidifier chamber 112 can be substantially circular in plan view. An inlet passage 134 and an exit passage 136 can be aligned or defined radially.

Gases enter the humidifier chamber 112 through the humidifier inlet port 115, and pass along the generally horizontal entry passage or inlet passage 134. The passage 134 is aligned radially towards the centre of the humidifier chamber 112.

Figure 14:
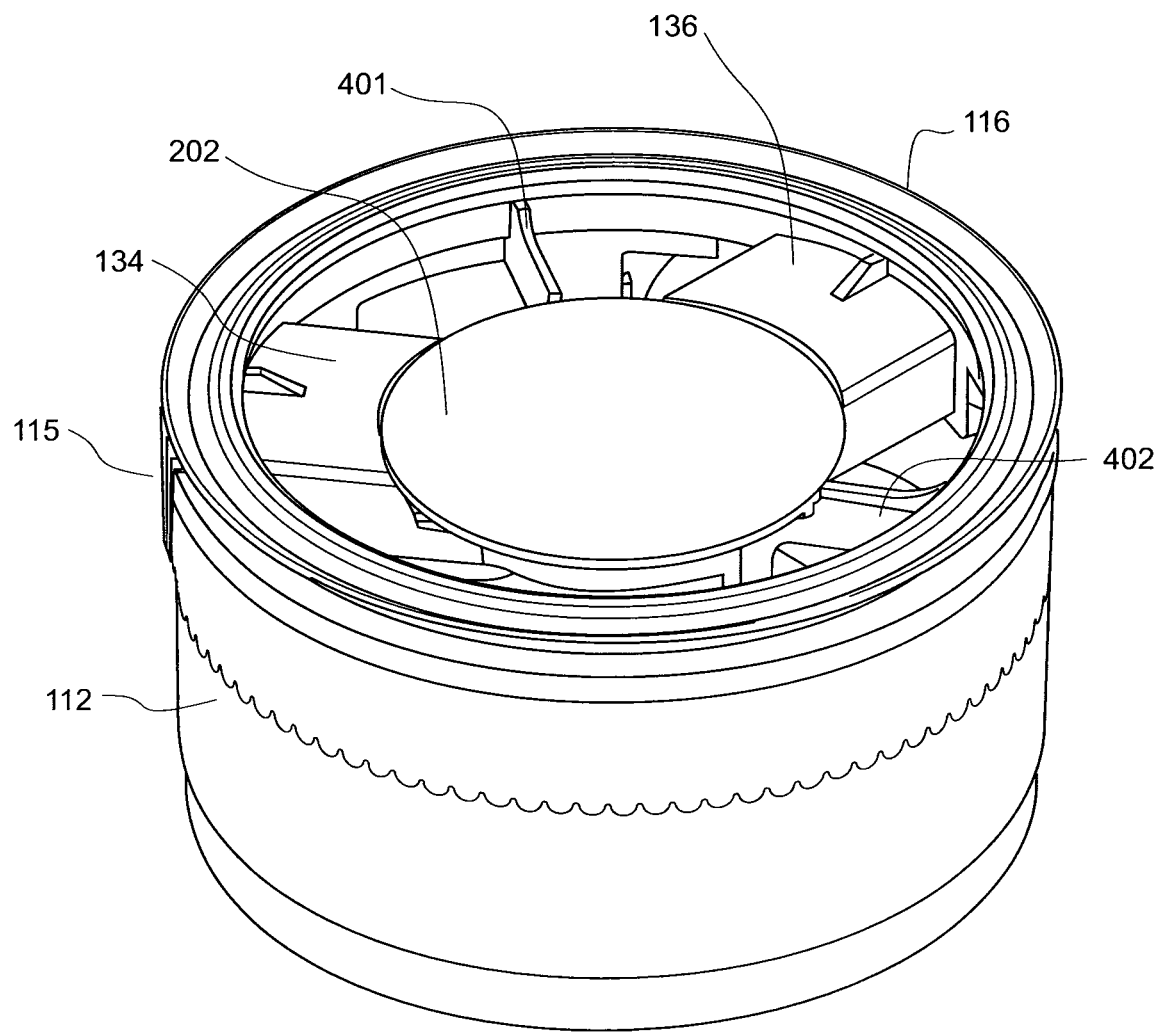
FIG. 14 shows a perspective view of the humidifier chamber of FIG. 13 with the humidifier chamber having a substantially horizontal inlet passage and an exit passage aligned radially and located towards the top of the chamber.
Figure 15:
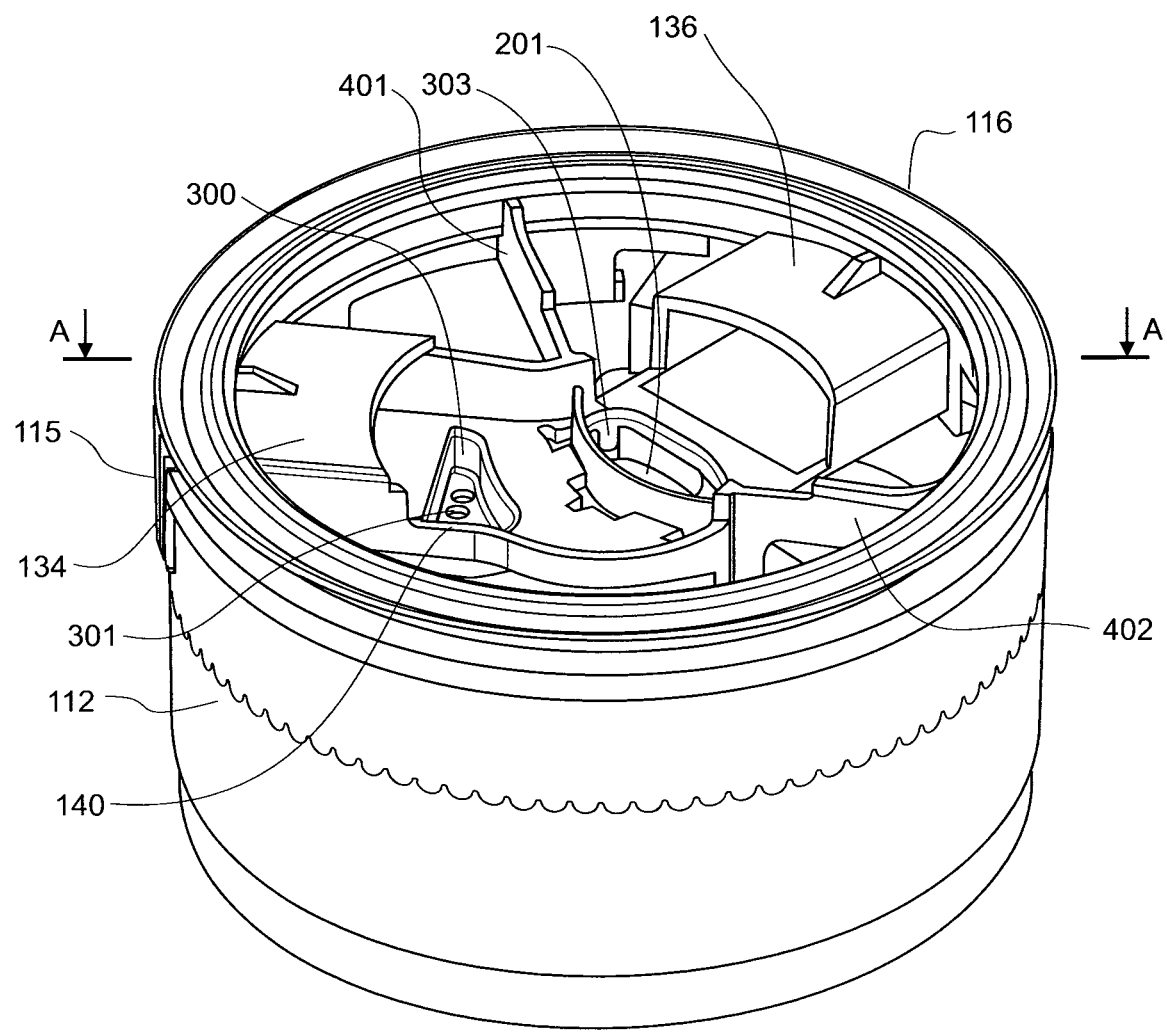
FIG. 15 shows the humidifier chamber of FIG. 14, but with a cap removed above open tops of the inlet and exit passages towards the centre of the chamber.
Figure 16:
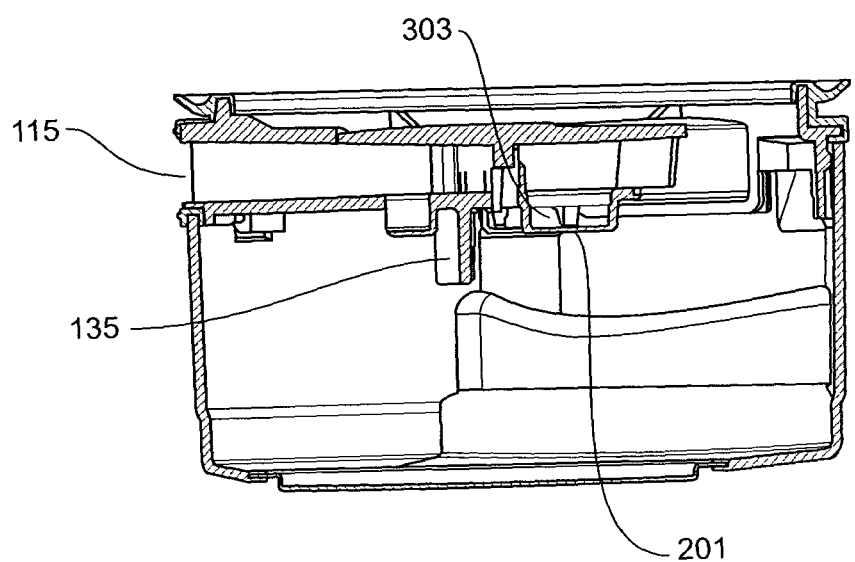
FIG. 16 shows a cutaway view of the chamber of FIG. 15, along section line A-A in FIG. 15.

As can best be seen with reference to FIGS. 14 and 15, the inlet passage 134 is open-topped at the end closest to the centre of the chamber. When assembled, the open top is closed by a removable cap 202. The cap 202 is formed as a removable item because this aids in manufacture and moulding of the chamber 112. Edges of the cap 202 also act as a handle, allowing a user to grip the cap and pull the chamber 112 out of the enclosure 42.

As best seen in FIG. 15, one portion 140 of the side of the inlet passage 134 is reduced in height. When the cap 202 is in position, there is an aperture in one side of the passage (i.e., between the portion 140 and the cap 202) to allow gases to exit the inlet passage 134 and to enter the main body of the chamber 112.

This aperture is referred to as the primary gases inlet aperture, as it allows gases to exit the inlet passage 134 and enter the main body of the chamber 112.

Also, an inlet passage recess 300 is formed in the lower surface or part of the passage 134 towards that end that is closest to the centre of the chamber 112. At least one or a number of secondary inlet apertures 301 are formed within the inlet passage recess 300, possibly on the lower part or surface, facing substantially vertically downwards into the humidifier chamber 112.

A proportion of the gases exit the inlet passage 134 through the entry apertures 301 and enter the main body of the humidifier chamber 112. The greater portion of the gases will exit into the main body of the chamber 112 through the primary inlet aperture, which is considerably larger than the secondary inlet apertures 301. However, the presence of the inlet recess 300 and secondary inlet apertures 301 is advantageous, as it forces at least a proportion of the gases entering the main body of the chamber 112 downwards towards the surface of the water, and increases the length of time that a given volume of gases will spend in the chamber such that the gases are more likely to be heated and humidified to the required level before exiting the chamber.

In use, the gases in the main body of the chamber 112 are heated and humidified, and exit the main body of the chamber 112, entering the exit passage 136. The exit passage is, in the exemplary embodiment, aligned radially, with one end at the centre of the chamber 112, connected to the end of the entry passage 134, the ends of the two passages are separated by an internal wall, so that in some embodiments, the passages are structurally connected but fluidically disconnected. The exit passage 136 has reduced height (or non-existent) side walls and an open top at that end that is closest to the centre of the chamber 112, as can best be seen with reference to FIG. 15. The cut out sides form primary gases exit apertures.

The exit passage 136 also includes an exit recess 303 formed in or on the lower surface of an exit passage 136. The exit recess has a secondary exit aperture or exit apertures 201. The apertures can be formed on the lower part or surface. The exit recess 303 and the secondary exit apertures 201 are, in some embodiments, formed at that end of the exit passage closest to the centre of the chamber 112. The secondary exit apertures 201 face substantially vertically downwards into the humidifier chamber 112. When fully assembled, the open top of the exit passage 136 is closed by the cap 202. Heated humidified gases from the chamber 112 enter the exit passage through the primary exit apertures in the sides of the passage, and through the exit apertures 201.

The majority of the gases enter the exit passage through the primary exit apertures in the side wall. The gases pass along the exit passage 136 to the chamber exit port 116 and then into the passage formed by the removable seal 32, and on to the user 3 as described above.

In some embodiments, the angle between the inlet passage 134 and the exit passage 136 is about 125 degrees between their centre lines, when viewed from above or in plan. The passages can be at an angle between 110 degrees and 160 degrees. This has the advantage that the fitting position of the chamber is easy to identify, and the chamber will only fit in the enclosure 42 in one orientation. Also, as the chamber inlet and outlet are in non-symmetrical positions, the chamber can't rotate once fitted.

As described above, both the inlet passage 134 and the exit passage 136 have recesses, an entry recess 300 and an exit recess 303 respectively, with secondary apertures formed in these recesses to allow a portion of the gases entering and exiting the chamber to pass through. Although the majority of the gases enter and exit the main body of the chamber 112 through the primary apertures formed in the sides of the passage, it has been found that forming these secondary apertures into the recesses is beneficial, as pressure drop across the chamber is minimised, and it is easier to produce and maintain the required amount of humidity. Also, water splash from the main part of the chamber into the passages is minimised or eliminated for a tilt angle of 20 degrees or under. This combination of features advantageously assists during standardisation testing. For example, the combination of features can assist in meeting the requirements of ISO 8185 clause 44.2, which states that "when the humidifier is tilted through 20 degrees in any direction from its normal operating position, there shall be no spillage of water from the liquid chamber or liquid reservoir into the breathing system when operated at the maximum flow . . . ".

As described above, the secondary entry apertures 301 and the secondary exit apertures 201 are formed in their respective recesses (300, 201) in their respective passages at a position towards the centre of the passages. Forming the recesses and apertures in the passages towards the centre of the chamber makes it more difficult for water in the chamber to enter the passages if a filled chamber is tilted in use—the likelihood of splashing occurring and water entering the exit passage 136 in particular is reduced. However, forming the entry apertures and the exit apertures in this manner means that they will be substantially adjacent to one another, and there is a risk that gases entering the chamber will not spend sufficient time in the chamber for them to become heated and humidified to the required levels (dwell time)—they may tend to cross over or short circuit between the entry and exit apertures before being suitably heated and humidified.

In order to ensure that the gases do not short circuit through the main body of the chamber and that they "dwell" for a suitable period within the chamber, the chamber includes a baffle 135 which extends downwards substantially vertically from the ends of the entry and exit passages, between the entry apertures and the exit apertures. In some embodiments, the baffle is also slightly curved horizontally, with the vertical edges curving towards the humidifier inlet port 115. It can be seen that the baffle 135 reduces the likelihood of air from the inlet passage 134 moving on a direct path to the exit passage 136.

As described above, the inlet passage 134 has a primary aperture on one side only. In some embodiments, this aperture is formed on that side of the passage that is furthest from the exit passage (i.e., the two passages being formed at an angle to one another as described above), and that therefore the gases have a further distance to travel before exiting the main body of the chamber 112, further reducing the likelihood of the gases "short-circuiting" through the chamber (the distance from the point at which the gases enter the chamber, to the nearest point at which they can exit, is maximised).

As can be seen in FIGS. 14 and 15, the chamber can also include buttress ribs 401, 402 extending radially outwards from substantially the centre or meeting point/join of the two passages, towards the periphery or perimeter of the chamber 112. The buttress ribs 401, 402 are located at the top of the main body of the chamber 112. The buttress ribs 401, 402 serve a dual purpose. Firstly, they strengthen the chamber against crushing forces applied from the sides (horizontally). Secondly, they deflect gases which are circulating at the top of the chamber downwards towards the surface of the water in the chamber. This helps to ensure that the gases in the chamber are suitably humidified before they exit the chamber.

In some embodiments, and in the embodiment shown in the figures, the humidifier gases inlet port 115 and the humidifier gases outlet port 116 are located on the perimeter of the chamber 112. In some embodiments, the chamber is circular in plan, so the perimeter is on the circumference. In an alternative form, the chamber can be configured so that one or both of the humidifier gases inlet port and the humidifier gases outlet port are located at a point or points closer to the centre of the chamber 112. For example, one or both of the passages 134, 136 could be shortened so that they only extend part of the way from the centre of the chamber to the perimeter. The humidifier gases inlet port and the humidifier gases outlet port in this configuration would be configured to connect to appropriate inlets and outlets on the blower or other external piece of equipment. The openings of the humidifier gases inlet port and the humidifier gases outlet port could open upwards, or horizontally, for example. The passage assembly or assemblies in this alternative configuration could be held in position by the buttress ribs 401, 402.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A gases modification unit for use as part of a breathing assistance system configured to provide heated humidified gases through a conduit to a user at a positive pressure for therapeutic purposes, comprising:
   an outer casing having an inlet vent or inlet port configured to admit gases into said outer casing in use, and an outlet port adapted for connection to said conduit in use, said outlet port configured to convey gases into said conduit, said inlet port and said outlet port connected by a gases path within said outer casing;
   electronic circuitry enclosed within said outer casing, said electronic circuitry adapted to provide at least one control signal configured to modify at least one property of gases passing along the gases path; and
   a conduit connection display which is adapted to indicate to a user that said conduit is correctly connected to said outlet port,
   wherein said gases modification unit is configured to establish that said conduit is correctly connected to said outlet port by receiving at least one signal indicative of air flow through said gases path and air pressure within said gases path, and confirming at least one stored value correlates with (i) the air flow through said gases path and (ii) the air pressure within said gases path.

2. A gases modification unit as claimed in claim 1 including a fan unit contained within said outer casing and located in said gases path, said fan unit adapted to receive said gases entering through said inlet vent or inlet port and provide a pressurised gases stream to said outlet port.

3. A gases modification unit as claimed in claim 1, wherein said conduit connection display comprises an LED (light emitting diode) located on said outer casing.

4. A gases modification unit as claimed in claim 3, wherein said LED is located on said outer casing at or close to said outlet port.

5. A gases modification unit as claimed in claim 1, wherein said gases modification unit further comprises a user display adapted to display information relating to operation of the gases modification unit, said conduit connection display incorporated as part of said user display.

6. A gases modification unit as claimed in claim 5, wherein said user display is adapted to display information regarding whether the gases modification unit is in an operating mode or an inactive mode.

7. A gases modification unit as claimed in claim 5, wherein said user display is adapted to display information regarding whether a removable peripheral device is correctly connected to the gases modification unit.

8. A gases modification unit as claimed in claim 1, wherein said gases modification unit further comprises a user display adapted to display information regarding whether the gases modification unit is in an operating mode or an inactive mode.

9. A gases modification unit as claimed in claim 1, wherein said gases modification unit further comprises a connection display adapted to display information regarding whether a removable peripheral device is correctly connected to the gases modification unit.

10. A gases modification unit as claimed in claim 1, wherein said conduit connection display is adapted to indicate to a user that said conduit is correctly connected to said outlet port independently of said electronic circuitry.

11. A gases modification unit as claimed in claim 1, wherein said gases modification unit further comprises a user display adapted to display a control menu including a plurality of options for controlling the gases modification unit, and wherein said electronic circuitry is configured to hide or block at least one of said options from access by a user.

12. A gases modification unit for use as part of a breathing assistance system configured to provide heated humidified gases through a conduit to a user at a positive pressure for therapeutic purposes, comprising:
an outer casing having an inlet vent or inlet port configured to admit gases into said outer casing in use, and an outlet port adapted for connection to said conduit in use, said outlet port configured to convey gases into said conduit, said inlet port and said outlet port connected by a gases path within said outer casing; and
a controller within said outer casing, said controller adapted to provide at least one control signal configured to control modification of at least one property of gases passing along the gases path;
wherein said controller is configured to determine that said conduit is correctly connected to said outlet port by receiving at least one signal indicate of air flow through said gases path and air pressure within said gases path, and confirming at least one stored value correlates with (i) the air flow through said gases path and (ii) the air pressure within said gases path and wherein said controller is configured to issue an indication that said conduit is correctly connected to said outlet port.

13. A gases modification unit as claimed in claim 12, further comprising a conduit connection display which is adapted to indicate to a user that said conduit is correctly connected to said outlet port.

14. A gases modification unit as claimed in claim 13, wherein said conduit connection display comprises an light emitting diode located on said outer casing.

15. A gases modification unit as claimed in claim 14, wherein said LED is located on said outer casing at or close to said outlet port.

16. A gases modification unit as claimed in claim 12, wherein said gases modification unit further comprises a user display adapted to display information relating to operation of the gases modification unit.

17. A gases modification unit as claimed in claim 12, further comprising a user display adapted to indicate to a user that said conduit is correctly connected to said outlet port and to display information relating to operation of the gases modification unit.

18. A gases modification unit as claimed in claim 12, wherein said gases modification unit further comprises a user display adapted to display information regarding whether the gases modification unit is in an operating mode or an inactive mode.

19. A gases modification unit as claimed in claim 12, wherein said gases modification unit further comprises a user display adapted to display a control menu including a plurality of options for controlling the gases modification unit, and wherein said controller is configured to hide or block at least one of said options from access by a user.

* * * * *